US007049102B1

(12) United States Patent
Van Gelder et al.

(10) Patent No.: US 7,049,102 B1
(45) Date of Patent: *May 23, 2006

(54) MULTI-GENE EXPRESSION PROFILE

(75) Inventors: Russell N. Van Gelder, Des Peres, MO (US); Mark E. Von Zastrow, San Carlos, CA (US); Jack D. Barchas, Philadelphia, PA (US); James H. Eberwine, Philadelphia, PA (US)

(73) Assignee: Board of Trustees of Leland Stanford University, Stanford, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/713,545

(22) Filed: Nov. 15, 2000

Related U.S. Application Data

(63) Continuation of application No. 09/286,533, filed on Apr. 5, 1999, now Pat. No. 6,291,170, which is a continuation of application No. 08/922,965, filed on Sep. 3, 1997, now Pat. No. 5,891,636, which is a continuation of application No. 08/636,748, filed on Apr. 19, 1996, now Pat. No. 5,716,785, which is a continuation of application No. 07/957,647, filed on Oct. 5, 1992, now Pat. No. 5,545,522, which is a continuation of application No. 07/411,370, filed on Sep. 23, 1989, now abandoned.

(51) Int. Cl.
C12P 19/34 (2006.01)
C07H 21/00 (2006.01)
C07H 21/02 (2006.01)
C07H 21/04 (2006.01)

(52) U.S. Cl. ............ 435/91.1; 536/23.1; 536/24.1
(58) Field of Classification Search .......... 536/23.1, 536/24.1; 435/91.1
See application file for complete search history.

(56) References Cited

U.S. PATENT DOCUMENTS

| | | |
|---|---|---|
| 3,077,780 A | 2/1963 | Takatsy |
| 3,252,331 A | 5/1966 | Lancaster |
| 3,531,258 A | 9/1970 | Merrifield |
| 4,353,989 A | 10/1982 | Bender |
| 4,357,421 A | 11/1982 | Emtage et al. |
| 4,362,699 A | 12/1982 | Verlander |
| 4,415,732 A | 11/1983 | Caruthers |
| 4,458,066 A | 7/1984 | Caruthers |
| 4,483,964 A | 11/1984 | Urdea |
| 4,500,707 A | 2/1985 | Caruthers |
| 4,503,151 A | 3/1985 | Paddock |
| 4,517,338 A | 5/1985 | Urdea |
| 4,562,157 A | 12/1985 | Lowe |
| 4,598,049 A | 7/1986 | Zelinka |
| 4,661,450 A | 4/1987 | Kempe et al. |
| 4,668,476 A | 5/1987 | Bridgham |
| 4,668,777 A | 5/1987 | Caruthers |
| 4,671,941 A | 6/1987 | Niina |
| 4,683,195 A | 7/1987 | Mullis |
| 4,683,202 A | 7/1987 | Mullis |
| 4,701,304 A | 10/1987 | Horn |
| 4,725,677 A | 2/1988 | Koster |
| 4,728,502 A | 3/1988 | Hamill |
| 4,738,669 A | 4/1988 | Vlock |
| 4,746,490 A | 5/1988 | Saneii |
| 4,748,002 A | 5/1988 | Neimark |
| 4,816,513 A | 3/1989 | Bridgham |
| 4,857,466 A | 8/1989 | Saunders |
| 4,861,866 A | 8/1989 | Durrum |
| 4,866,166 A | 9/1989 | Wigler |
| 4,882,127 A | 11/1989 | Rosenthal |
| 4,923,901 A | 5/1990 | Koester |
| 4,959,313 A | 9/1990 | Taketo |
| 4,965,188 A | 10/1990 | Mullis et al. |
| 4,973,679 A | 11/1990 | Caruthers |
| 4,981,783 A | 1/1991 | Augenlicht |
| 4,987,783 A | 1/1991 | Augenlicht |
| 5,019,348 A | 5/1991 | Ohms |
| 5,021,335 A | 6/1991 | Tecott et al. |
| 5,043,272 A * | 8/1991 | Hartley et al. ............. 435/91 |
| 5,057,410 A | 10/1991 | Kawasaki |
| 5,073,495 A | 12/1991 | Anderson |
| 5,085,983 A | 2/1992 | Scanlon |
| 5,106,585 A | 4/1992 | Minami |
| 5,112,575 A | 5/1992 | Whitehouse |
| 5,112,734 A * | 5/1992 | Kramer et al. ............. 435/6 |

(Continued)

FOREIGN PATENT DOCUMENTS

EP     0052002     5/1982

(Continued)

OTHER PUBLICATIONS

Abbott et al. Enzymatic gene amplification: Qualitative and quantitative methds fo detecting proviral DNA amplified in vitro. J. Infect. Diseases vol. 158(6):1158-1169, 1988.*

(Continued)

*Primary Examiner*—James Ketter
*Assistant Examiner*—Konstantina Katcheves
(74) *Attorney, Agent, or Firm*—Barbara J. Luther; The Luther Law Firm

(57) ABSTRACT

This invention relates to the use of promoters for ribonucleic acid amplification and other genetic manipulations. Processes are provided wherein complementary deoxyribonucleic acid (cDNA) is synthesized from a ribonucleic acid (RNA) sequence using a complementary primer linked to an RNA polymerase promoter region complement and then anti-sense RNA (aRNA) is transcribed from the cDNA by introducing an RNA polymerase capable of binding to the promoter region. Additional processes using the resulting aRNA are also described.

12 Claims, 1 Drawing Sheet

U.S. PATENT DOCUMENTS

| | | | |
|---|---|---|---|
| 5,112,736 | A | 5/1992 | Caldwell |
| 5,122,457 | A | 6/1992 | Reim |
| 5,130,238 | A | 7/1992 | Malek et al. |
| 5,132,418 | A | 7/1992 | Caruthers |
| RE34,069 | E | 9/1992 | Koster |
| 5,143,854 | A | 9/1992 | Pirrung |
| 5,174,962 | A | 12/1992 | Brennan |
| 5,175,103 | A | 12/1992 | Lee |
| 5,175,209 | A | 12/1992 | Beattie |
| 5,198,368 | A | 3/1993 | Khalil |
| 5,221,518 | A | 6/1993 | Mills |
| 5,281,519 | A | 1/1994 | Schechter |
| 5,348,855 | A | 9/1994 | Dattagupta |
| 5,384,261 | A | 1/1995 | Winkler |
| 5,399,491 | A | 3/1995 | Kacian |
| 5,409,818 | A | 4/1995 | Davey |
| 5,437,990 | A | 8/1995 | Burg et al. |
| 5,459,037 | A | 10/1995 | Sutcliffe |
| 5,466,788 | A * | 11/1995 | Ahlquist et al. ............ 536/24.1 |
| 5,487,970 | A | 1/1996 | Rowley |
| 5,489,678 | A | 2/1996 | Fodor |
| 5,514,545 | A | 5/1996 | Eberwine |
| 5,554,517 | A | 9/1996 | Davey |
| 5,569,584 | A | 10/1996 | Augenlicht |
| 5,622,820 | A | 4/1997 | Rossi |
| 5,665,547 | A | 9/1997 | Pardee |
| 5,716,785 | A | 2/1998 | Van Gelder et al. |
| 5,783,391 | A | 7/1998 | Rossi |
| 5,869,249 | A | 2/1999 | Rossi |
| 5,888,779 | A | 3/1999 | Kacian |
| 6,054,270 | A | 4/2000 | Southern |

FOREIGN PATENT DOCUMENTS

| | | |
|---|---|---|
| EP | 0062971 | 10/1982 |
| EP | 0118977 | 9/1984 |
| EP | 0158892 | 10/1985 |
| EP | 0173378 | 3/1986 |
| EP | 0176916 | 4/1986 |
| EP | 0186069 | 7/1986 |
| EP | 0195303 | 9/1986 |
| EP | 0197558 | 10/1986 |
| EP | 0200362 | 12/1986 |
| EP | 0206769 | 12/1986 |
| EP | 0207459 | 1/1987 |
| EP | 0219814 | 4/1987 |
| EP | 0271824 | 6/1988 |
| EP | 0281391 | 9/1988 |
| EP | 0282185 | 9/1988 |
| EP | 0289479 | 11/1988 |
| EP | 0320148 | 6/1989 |
| EP | 0329822 | 8/1989 |
| EP | 0373960 | 6/1990 |
| EP | 06236831 | 11/1994 |
| WO | WO 88/01302 | 2/1988 |
| WO | WO88/10315 | 12/1988 |
| WO | WO89/01050 | 2/1989 |
| WO | WO 89/06700 * | 7/1989 .................... 435/6 |
| WO | WO 90/06995 | 6/1990 |

OTHER PUBLICATIONS

Kwoh et al. Transcription-based amplificatoin system and detection of amplified human immunodeficiency virus type 1 with a bead-based sandwich hybridization format. PNAS vol. 86:1173-1177, 1989.*

Gingeras et al. Transcription-based amplification system and the detection of its RNA products by a bead-based sandwich hybridization system. J. Cell. Biochem. (Suppl. 13E, 286), 1989.*

Gilliland et al. Quantitative amplication of mRNA using polymerase chain reaction. J. Cell. Biochem. (Suppl. 13E, 270), 1989.*

Hougaard, Bolund, Fujiwara, Larsson. Endogenous polyamines are intimately associated with highly condensed chromatin in vivo. A flourescene cytochemical and immunocytochemical study ofspermidine during the cell cycle and in reactivated nuclei. Eur J Cell Biol 44: (1987).

Hindkjaer, Kock, Mogensen, Kolvraa, and Bolund. Primed In Situ (PRINS) Labeline of DNA. Methods in Molecular Biology, vol. 33 1994. pp 95-107.

Mogensen, Paderseen, Hindkjaer, Kolvraa, Bolund. Primed in Situ (PRINS) Labeling of RNA. Methods in Molecular Biology vol. 33 1994. pp. 256-275.

Koch, Hindjaer, Kolvraa, Bolund. Construction of a Panel of Chromosome-specific oligonucleotide probes (PRINS-primers) useful for the identification of individual human chromosomes in situ. Cytogenet Cell Genet 71:142-147, 1995.

Kock, hindkjaer, Mogensen, Kolvraa, and Bolund. An Improved Method for Chromosome-Specific Labeling of a Satelite DNA in situ by Using Denatured Double-Stranded DNA in situ Labeling (PRINS) Procedure. GATA pp. 171-178, 1991.

Terkelsen, Koch, Kolvraa, Hindkjaer, Pedersen, and Bolund. Repeated primed in situ labeling:formation and labeling of specific DNA sequences in chromosomes and nuclei. Cytogenet Cell Genet 63: 235-237 (1993).

Hinds, Ashley, Sutcliffe, Nelson, Warren, Housman, and Schalling. Tissue specific expression of FMR-1 provides evidence for a functional role in fragile X syndrome. Nature genetics vol. 3. Jan. 1995 pp. 36-43.

Gething, Bye, Skehel, Waterfield, Cloning and DNA sequence of double-stranded copies of haemagglutinin genes from H2 and H3 strands elucidates antigenic shift and drift in human influenza virus. Nature vol. 287 Sep. 1980 pp. 301-306.

Mogensen, Kolvraa, Hindkjaer, Petersen, Kock, Nygard, Jensen, Gregersen, Junker, and Bolund. Nonradioactive, Sequence-Specific Detection of RNA in Situ by Primed in Situ Labeling (PRINS). Experimental Cell Research 196, pp. 92-98 (1991).

Kelso, troutt, Maraskovsky, Gough, Morris, Pech, Thomson. Heterogeneity in Lymphokine Profiles of CD4+ and CD8+ T Cells and Clones Activated in vivo and in Vitro. Immunolocical Reviews 1991 No. 123 pp. 85-114.

VonZastrow, Barchas, Eberwine. An Approach to the Molecular Biology of Oplate Tolerance: Identification of Opiate-Regulated Transcripts. NIDA Res Monogr 111: 85-95 (1991).

Adams, Kelley, Gocayne, Dubnick, Polymeropoulos, Xiao, Merril, Wu, Olde, Moreno, Kerlavage, McCombie, Venter. complementary DNA Sequencing: Expressed Sequence Tags and Human Genome Project. Science vol. 252 (1991)pp. 1651-1656.

Meyers, Gumerlock, Kawasaki, Wang, White, Erlich. Bladder Cancer- Human Leukocyte Antigen II, Interleukin-6, and Interleukin- 6 Receptor Expression Determined by the Polymerase Chain Reaction. Cancer, vol. 67, (1991) pp. 2087-2095.

Mackler, Eberwine. The Molecular Biology of Addictive Drugs. Molecular Neurobiology vol. 5 1991. pp. 45-58.

Okubo, Hori, Matoba, Niiyama, Fukushima, Kojima, Matsubara. Large Scale cDNA sequencing for analysis of quantitative and qualitative aspects of gene expression. Nature Genetics vol. 2 (1992) pp. 173-179.

Mackler, Brooks, Eberwine. Stimulus-Induced Coordinate Changes in mRNA Abundance in Single Postsynaptic Hippocampal CA1 Neurons. Neuron. vol. 9 pp. 539-548 (1992).

Liang, Pardee. Differential Display of Eukaryotic Messenger RNA by Means of the Polymerase Chain Reaction, Science vol. 257, Aug. (1992) pp. 967-971.

Liang, Averboukh, and Pardee. Distribution and cloning of eukaryotic mRNAs by means of differential display: refinements and optimization. Nucleic Acids Reasearch, 1993 vol. 21, No. 14. pp. 3269-3275.

Mackler, Eberwine, Diversity of Glutamate Receptor Subunit mRNA Expression within Live Hippocampal CA1 Neurons. Molecular Pharmacology, (1993) 44: pp. 308-315.

Pekarek, Weichselbaum, Beckett, Nachman, Schreiber. Footprinting of Individual Tumors and Their Variants by Constitutive Cytokine Expression Patterns. Cancer Research 53, 1978-1981 May, 1993.

Jaakkola, Peltonen, Riccardi, Chu, Uitto, Type 1 neurofibromatosis: selective expression of extracellular matrix genes by Schwann cells, perineurial cells, and fibroblasts in mixed cultures. J Clin Invest 84: (1989) pp. 253-261.

Belldegrun, Kasid, Uppenkamp, Topalian, Rosenberg. Human tumor infiltration lymphocytes. Analysis of lymphokine mRNA expression and relevance to cancer immunotherapy. J Imminol 142; 4520-6, 1989, pp. 4520-4526.

Haung and Hershey. Translational initiation factor expression and ribosomal protein gene expression are repressed coordinately but by different mechanisms in murine lymphosarcoma cells treated with glucocorticoids. Mol Cell Biol 9, 1989 pp. 3679-3684.

Kock, Kolvraa, Hobolt, Petersen, Willard, Waye, Gregersen, and Bolund. A case of 46, XX,r(X)(p1q1) diagnosed by in situ hybridization. Clinical Genetics (1990) 37; 216-220.

Koch, Kolvraa, Hertz, Rasmussen, Gregersen, Fly, And Bolund. In situ hybridization analysis of isodicentric X-chromosomes with short arm fusion. Clinical Genetics (1990) 37: pp. 450-455.

Belldegrun, Kasid, Uppenkamp, and Rosenberg. Lymphokine mRNA profile and functional analysis of human CD4+ clone with unique antitumor specificity isolated from renal cell carcinoma ascitic fluid. Cancer Immunol Immunother (1990) 31: pp. 1-10.

Quantatative analysis of cytokine gene expression in rheumatoid arthritis. Firestein, Garcia, Maki. , Journal of Immunology 144: 1990, pp. 3347-3353.

Albrecht E. Sipple, Purification and Characterization of Adenosine Triphosphate: Ribonucleic Acid Adenyltranfeerase grom *Escherichia coli*. Eur. J. Biochem. 37, 31-40, 1973.

Hastie, and Bishop. The Expression of Three Abundance Classes of Messenger RNA in Mouse Tissue. Cell. vol. 9. pp. 761-774 Dec. 1976.

Bentle, And Hahn. Complexity and Characterization of Polyadenylated RNA in the Mouse Brain. Cell. vol. 8, pp. 139-150 May 1976.

Dona M. Chikaraishi, Complexity of Cytoplasmic Polyadenylated and Nonpolyadenylated Rat Brain Ribonucleic Acids. Biochemistry 1979. vol. 18, No. 15, pp. 3249-3256.

Milner, Sutcliffe. Gene Expression in Rat Brain. Nucleic Acid Research 1983, vol. 11, pp. 5497-5521.

Richard E. Harlan. Regulation of Neuropeptide Gene Expression by Steroid Hormones. Molecular Neurobiology vol. 2, 1988. pp. 183-200.

J. Gregor Sutcliffe. mRNA in the mammalian central nervous system. Ann. Rev. Neurosci. 1988, pp. 157-189.

Ansorge, Rosenthal, Sproat, Schwager, Stegemann, Voss. Nucleic Acid Research. vol. 16 No. 5 1988, pp. 2203-2206.

Mattson, Kater, Development and selective neurodegeneration in cell cultures from different hippocampal regions. Brain Reasearch, 490 (1989) pp. 110-125.

Lightman and Young. Corticotrophin-Releasing Factor, Vasopressing and Pro-Opiomelanocortin mRNA Responses to Stress and Opiates in the Rat. Journal Physiology (1988)403, pp. 511-523.

Uhl, Ryan, Schwartz. Morphine alters preproenkephalin gene expression. Brain Res. 1988 vol. 459(2): 391-7.

James, Pearce. The Influence of Adjuvant on Induction of Protective Immunity By A Non-Living Vassine Against Schistosomiasis. J. Immunology, vol. 140 No. 8 (1989) pp. 2753-2759.

North and Williams. On the Potassium Conductance Increased by Opiods In Rat Locus Coeruleus Neurones. J. Physiol. (1985), 364, pp. 265-280.

Himill, Neher, Sakmann, and Sugworth. Improved Patch-Clamp Techniques for High-Resolution Current Recording from Cells and Cell-Free Membrane Patches. Pflugers Archive (1981) 391: 85-100.

Perozzi, Mengheri, Fafaonio, Gaetani. Expression of liver genes coding for plasma proteins in protein deficiency. FEBS Letters, vol. 257, No. 2, Nov. 1989. pp. 215-218.

Van Gelder, Zastrow, Yool, Dement, Barchas, Eberwine, Amplified RNA sythesized from limited quantities of heterogeneous cDNA. Proc. Natl. Acad. Sci. USA, vol. 87. pp. 1663-1667. Mar. 1990.

Guitart, Hayward, Nisenbaim, Johnson, Haycock, Nestler. Identification, of MARPP-58, A Morphine- and Cyclic AMP-Regulated Phosphoprotein of 58 kDa, as Tyrosine Hydroxylase: Evidence for Regulation of its Expression by Chronic Morphine in the Rat Locus Coeruleus. The Journal of Neuroscience, Aug., 1990, 10(8): 2649-2659.

Hayward, Duman, Nestler. Induction of the c-fos proto-oncogene during opiate withdrawal in the locus coeruleus and other regions of rat brain. Brain Reasearch, 525 (1990) pp. 256-266.

Eberwine, Yeh, Miyashiro, Cao, Nair, Finnell, Zettel, Coleman, Analysis of gene expression in single live neurons. Proc. Natl. Acad Sci. USA. vol. 89. pp. 3010-3014, Apr. 1992.

Okayama, H., et al., "High-efficiency cloning of full-length cDNA", article, Mollecular and Cellular Biology, V 2, N 2, p. 161-170, Feb. 1982.

Arcturus Systems for Microgenomics, "RiboAmp RNA Amplification Kit, Amplify RNA with the Highest Fidelity", brochure, p. 1-6, 2002.

Arcturus Systems for Microgenomics, "RiboAmp RNA Amplification Kit", User Guide, Catalog #KIT0201, p. 1-45., 2002.

Sambrook, J., et al., "Molecular Cloning", Laboratory Manual, ARC 000444, Second Edition, Cold Spring Harbor Laboratory Press, Cold Spring Harbor, NY, C 8, p. 8.2-.86, 1989.

Sargent, T., "Isolation of differentially expressed genes", article, Methods of Enzymology, V 152, Academic Press, Inc., p 423-32, 1987.

Sarkar, G., et al., "Access to a messenger RNA sequence or its protein product is not limited by tissue or species specificity", article, Science, V 244, p. 331-334, Apr. 21, 1989.

Stoflet, E., et al., "Genomic amplification with transcript sequencing", article, Science, V 239, p. 491-4, Jan. 29, 1988.

Butler, E.T. et al. "Bacteriophage SP6-specific RNA Polymerase," (1982) J. of Biol. Chem. 257(10): 5772-5778.

Cha, T. et al. "Studies of the DNA Helicase-RNA Primase Unit from Bacteriophage T4," (1986) J. of Biol. Chem. 261(15): 7001-7010.

Chu, B.C.F. et al. "Synthesis of an Amplifiable Reporter RNA for Bioassays," (1986) Nucleic Acids Res. 14(14): 5591-5603.

Coutlee, F. et al. "Immunodetection of DNA with Biotinylated RNA Probes: A Study of Reactivity of a Monoclonal Antibody to DNA-RNA Hybrids," (1989) Analytical Biochem. 181 96-105.

Cova, L. et al. "Use of cRNA Probes for the Detection of Enteroviruses by Molecular Hybridization," (1988) J. of Med. Virology 24: 11-18.

Dalessio, J.M. et al. "Second-Strand cDNA Synthesis with *E. coli* DNA Polymerase I and RNase H: The Fate of Information at the mRNA 5' Terminus and the Effect of *E. coli* DNA Lioase." (1988) Nucleic Acids Res. 16(5): 1999-2014.

Dean, R.R. et al. "Narcolepsy Without Unique MHC Class II Antigen Association: Studies in the Canine Model," (1989) Human Immunology 25: 27-35.

Deiniger, P.L. "Full-Length cDNA Clones: Vector-Primed cDNA Synthesis," (1987) In Methods in Enzymology vol. 152 Guide to Molecular Cloning, Berger, S.L. et al. eds Academic Press Inc San Diego pp. 371-389.

Denny, P. et al. "Oligo-Riboprobes," (1988) Histochemistry 89: 481-483.

Devos, R. et al. (1988). "Slippage of DNA Polymerase I During Synthesis of ds-cDNA," (1988) Nucleic Acids Res. 16(4): 1630.

Dunn, T.J. et al. "Phenobarbital-Inducible Aldehyde Dehydrogenase in the Rat," (1989) J. of Biol. Chem. 264(22): 13057-13065.

Eberwine, J.H. et al. "Glucocorticoid Regulation of Pro-Opiomelanocortin Gene Transcription in the Rat Pituitary," (1984) J. of Biol. Chem. 269(4): 2166-2170.

Eberwine, J.H. et al. "Isolation of Enzyme cDNA Clones by Enzyme Immunodetection Assay: Isolation of a Peptide Acetyltransferase," (1987) Proc. Natl. Acad. Sci. USA 84: 1449-1453.

Endo, F. et al. "Primary Structure and Gene Localization of Human Prolidase," (1989) J. of Biol. Chem. 264(8): 4476-4481.

Feinberg, A.P. et al. "A Technique for Radiolabeling DNA Restriction Endonuclease Fragments to High Specific Activity," (1983) Analytical Biochem. 132: 6-13.

Foster, J.L. et al. "Cloning, Sequence, and Expression of the Drosophila cAMP-Dependent Protein Kinase Catalytic Subunit Gene," (1988) J. of Biol. Chem. 263(4): 1676-1681.

Foutz, A.S. et al. "Genetic Factors in Canine Narcolepsy," (1979) Sleep. 1(4): 413-422.

Fradkin, L.G. et al. "Primer-Dependent Eukaryotic RNA Polymerase Capable of Accurate Transcription from the Adenovirus Major Late Promoter in a Reconstituted System," (1985) Proc. Natl. Acad. Sci. USA 82: 7979-7983.

Frech, G.C. et al. "Construction of Directional cDNA Libraries Enriched for Full-Length Inserts in a Transcription-Computer Vector,"(1989) (PubMed Abstract) Gene Anal. Tech. 6(2): 33-38.

Frohman, M.A. et al. "Rapid Production of Full-Length cDNAs from Rare Transcripts: Amplification Using a Single Gene-Specific Oligonucleotide Primer," (1988) Proc. Natl. Acad. Sci. USA 85: 8998-9002.

Fuller, C.W. et al. "Initiation of DNA Replication at the Primary Origin of Bacteriophage T7 by Purified Proteins," (1985) J. of Biol. Chem. 260(5): 3185-3196.

Gaubatz, J. et al. "Strategies for Constructing Complementary DNA for Cloning," (1982) J. Theor. Biol. 95: 679-696.

Gaubatz, J. et al. (1985). "Displacement Synthesis of Globin Complementary DNA: Evidence for Sequence Amplification," (1985) Biochimica et Biophysica Acta 825: 175-187.

Gingeras, T.R. et al. "Nucleotide Sequences from the Adenovirus-2 Genome," (1982) J. of Biol. Chem. 267(22): 13475-13491.

Gingeras, T.R. et al. (1987). "Hybridization Properties of Immobilized Nucleic Acid," (1987) Nuc. Acids Res. 15(13) 5373-5390.

Goodman, T.C. et al. "Effects of Neighboring DNA Homopolymers on the Biochemical and Physical Properties of the *Escherichia coli* Lactose Promoter," (1982) J. of Biol. Chem. 257(21): 12970-12978.

Gopalakrishna, Y. et al. "The Synthesis of DNA Complementary to Polyadenylate-Containing RNA for Bacillus Subtilis," (1982) J. of Biol. Chem. 257(6): 2747-2750.

Gould, S.J. et al. (1989). "Use of the DNA Polymerase Chain Reaction for Homology Probing: Isolation of Partial cDNA or Genomic Clones Encoding the Iron-Sulfur Protein of Succinate Dehydrogenase from Several Species," (1989) Proc. Natl, Acad. Sci. USA 86: 1934-1938.

Gruol, D.L. et al. "Multiple Voltage-Sensitive K+ Channels Regulate Dendric Excitability in Cerebellar Purkinje Neurons," (1989) (PubMed Abstract) Neurosci. Lett. 97(1-2): 97-102.

Guatellli, J.C. et al. "Nucleic Acid Amplification In Vitro: Detection of Sequences with Low Copy Numbers and Application to Diagnosis of Human Immunodeficiency Virus Type 1 Infection," (1989) Clin. Microbiol. Revs. 2(2): 217-226.

Gubler, U. et al. (1983). "A Simple and Very Efficient Method for Generating cDNA Libraries," (1983) Gene 25: 263-269.

Gubler, U. et al. "Second-Strand cDNA Synthesis: Classical Method," (1987) In Methods in Enzymology vol. 152 Guide to Molecular Cloning, Berger, S.L. et al. eds., Academic Press, Inc., San Diego. pp. 325-335.

Haas, R.C. et al. "Isolation and Characterization of the Gene and cDNA Encoding Human Mitochondrial Creatine Kinase," (1989) J. of Biol. Chem. 264(5): 2890-2897.

Hagen, F.S. et al. "Assaying the Quality of cDNA Libraries," (1988) BioTechniques. 6(4): 340-345.

Heidecker, G. et al. "Sequence Analysis of zein cDNAs Obtained by an Efficient mRNA Cloning Method," (1983) Nucleic Acids Res. 11(14): 4891-4906.

Hinton, D.M. et al. "Bacteriophage T4 DNA Primase-Helicase," (1987) J. of Biol. Chem. 262(22): 10873-10878.

Hohn, P.A. et al. "Genomic Organization and Chromosomal Localization of the Human Cathepsin G Gene," (1989) J. of Biol. Chem. 264(23): 13412-13419.

Holloman, J.D. et al. "HLA-DR Restriction-Fragment-Length Polymorphisms in Narcolepsy," (1987) J. of Neurosci. Res. 18:239-244.

Horwitz, M.S.Z. et al. "DNA Sequences of Random Origin as Probes of *Escherichia coli* Promoter Architecture," (1988) J. of Biol. Chem. 263(29): 14724-14731.

Huang, B. et al. "Molecular Cloning of cDNA for Caltractin, a Basal Body-Associated Ca2+ -Binding Protein: Homology In Its Protein Sequence with Calmodulin and the Yeast CDC31 Gene Product," (1988) J. of Cell Biol. 107: 133-140.

Huber, H.E. et al. "Interaction of Mutant Thioredoxins of *Escherichia coli* with the Gene 5 Protein of Phage T7," (1986) J. of Biol. Chem. 261(32): 15006-15012.

Huber, H.E. et al "*Escherichia coli* Thioredoxin Stabilizes Complexes of Bacteriophage T7 DNA Polymerase and Primed Templates," (1987) J. of Biol. Chem. 282(33): 16224-16232.

Huber, H.E. et al. "Human Immunodeficiency Virus 1 Reverse Transcriptase," (1989) J. of Biol. Chem. 264(8): 4669-4678.

Joels, M. et al. "Unique Properties of Non-N-Methyl-D-Aspartate Excitatory Responses in Cultured Purkinje Neurons," (1989) (PubMed Abstract) Proc. Natl. Acad. Sci. USA 86(9): 3404-3408.

Joyce, G.F. "Amplification, Mutation and Selection of Catalytic RNA," (1989) Gene 82: 83-87.

Joyce, G.F. "Building the RNA World: Evolution of Catalytic RNA in the Laboratory," (1989) Molecular Biol. of RNA, 361-371.

Karpel, R. et al.. "Sequencing of the Gene ant Which Affects the Na+/H+ Antiporter Activity in *Escherichia coli*," (1988) J. of Biol. Chem. 263(21): 10408-10414.

Kassavetis, G.A. et al. "Bacteriophage SP6-Specific RNA Polymerase," (1982) J. of Biol. Chem. 257(10): 5779-5788.

Keohavong, P. et al. "Laboratory Methods: DNA Amplification In Vitro Using T4 DNA Polymerase," (1988) NA 7: 63-70.

Klein, R.D. et al. "Effects of Neighboring DNA Homopolymers on the Biochemical and Physical Properties of the *Escherichia coli* Lactose Promoter," (1982) J. of Biol. Chem. 257(21): 12954-12961.

Kotani, H. et al. "Nucleotide Sequence and Expression of the Cloned Gene of Bacteriophage SP6 RNA Polymerase," (1987) Nucleic Acids Res. 15(6): 2653-2664.

Krieg, P.A. et al. "Functional Messenger RNAs Are Produced by SP6 In Vitro Transcription of Cloned cDNAs," (1984) Nucleic Acids Res. 12(18): 7057-7070.

Krupp, G. "RNA Synthesis: Strategies for the Use of Bacteriophage RNA Polymerases," (1988) Gene 72: 75-89.

Krupp, G. et al. "Simplified In Vitro Synthesis of Mutated RNA Molecules," (1987) Federation of European Biochemical Societies 212(2): 271-275.

Land, H. et al. "5'-Terminal Sequences of Eucaryotic mRNA Can Be Cloned with High Efficiency," (1981) Nucleic Acids Res. 9(10): 2251-2266.

Lang, K.M. et al. "Cloning Specific Complete Polyadenylylated 3'-Terminal cDNA Segments," (1985) Gene 33: 191-196.

Levy, A. et al. "Distamycin Paradoxically Stimulates the Copying of Oligo(dA)-Poly(dT) by DNA Polymerases," (1989) Biochemistry 28: 7262-7267.

Liao, C. et al. "Molecular Cloning and Expression of a Fifth Muscarinic Acetylcholine Receptor," (1989) J. of Biol. Chem. 264(13): 7328-7337.

Lindenbaum, J.O. et al. "The Adenovirus DNA Binding Protein and Adenovirus DNA Polymerase Interact to Catalyze Elongation of Primed DNA Templates," (1986) J. of Biol. Chem. 261(22): 10218-10227.

Lizardi, P.M. et al. "Exponential Amplification of Recombinant-RNA Hybridization Probes," (1988) Biotechnology 6: 1197-12202.

Loewy, Z.G. et al. "Site-Directed Transcription Initiation with a Mobile Promoter," (1989) Gene 83: 367-370.

Lomell, H. et al. "Quantative Assays Based on the Use of Replicatable Hybridization Probes," (1989) Clin. Chem. 35(9): 1826-1831.

Lopez-Casillas, F. et al "Heterogeneity at the 5' End of Rat Acetyl-Coenzyme A Carboxylase mRNA," (1989) J. of Biol. Chem. 264(13): 7176-7184.

Lu, X. et al. "Construction and Quality of cDNA Libraries Prepared from Cytoplasmic RNA Not Enriched in Poly(A)+RNA," (1988) Gene 71: 157-164.

Lu, X. et al. "Cell Cycle Phase-Specific cDNA Libraries Reflecting Phase-Specific Gene Expression of Ehrlich Ascites Cells Growing in Vivo," (1988) Experimental Cell Res. 174: 199-214.

Mayr, V. A. "TC-Marker des Attenuierten Vaccinia-Impfstammes "MVA" in Menschlichen Zellkulturen," (1976) Zbl. Vet. Med. B. 23: 417-430.

Mead, D.A. et al. "Single-Stranded DNA 'Blue' T7 Promoter Plasmids: A Versatile Tandem Promoter System for Cloning and Protein Engineering," (1986) Protein Engineering 1(1): 67-74.

Melton, D.A. et al. "Efficient in vitro Synthesis of Biologically Active RNA and mRNA Hybridization Probes from Plasmids Containing a Bacteriophage SP6 Promoter," (1984) Nucleic Acids Res. 12(18): 7035-7056.

Mifflin, T.E. "Use and Application of Nucleic Acids Probes in the Clinical Laboratory," (1989) Clinical Chemistry 35(9): 1819-1825.

Milligan, J.E. et al. "In Vitro Transcription of Synthetic DNA Using T7 RNA Polymerase," (1987) In RNA Processing: Abstracts of Papers Presented at the 1987 Meeting on May 13-May 17, 1987. Arranged by Cech, T et al., Cold Spring Harbor Laboratory: Cold Spring Harbor, NY, p. 1.

Milligan, J.F. et al. "Oligoribonucleotide Synthesis Using T7 RNA Polymerase and Synthetic DNA Templates," (1987) Nucleic Acids Res. 15(21): 8783-8798.

Milligan, J.F. et al. "Synthesis of Small RNAs Using T7 RNA Polymerase," (1989) Methods In Enzymol. 180: 51-62.

Milner, R.J. et al. "Gene Expression in Rat Brain," (1983) Nucleic Acids Res. 11(16): 5497-5520.

Motoyama, M. et al. "Restriction Fragment Length Polymorphism in Canine Narcolepsy," (1989) Immunogenetics 29: 124-126.

Murakawa, G.J. et al. "Laboratory Methods—Direct Detection of HIV-1 RNA from AIDS and ARC Patient Samples," (1988) DNA 7(4): 287-295.

Nakai, H. et al "Interactions of the DNA Polymerase and Gene 4 Protein of Bacteriophage T7," (1986) J. Of Biol. Chem. 261(32): 15208-15216.

Nakai, H. et al. "Dissection of RNA-Primed DNA Synthesis Catalyzed by Gene 4 Protein and DNA Polymerase of Bacteriophage T7," (1986) J. of Biol. Chem. 261(32): 15217-15224.

Nakai, H. et al. "Leading and Lagging Strand Synthesis at the Replication Fork of Bacteriophage T7," (1988) J. of Biol. Chem. 263(20); 9818-9830.

Nakai, H. et al. "The Effect of the T7 and *Escherichia coli* DNA-Binding Proteins at the Replication Fork of Bacteriophage T7," (1988) J. of Biol. Chem. 263(20): 9831-9839.

Noma, Y. et al. "Cloning of cDNA Encoding the Murine IgG1 Induction Factor by a Novel Strategy Using SP6 Promoter," (1986) Nature 319: 640-646.

O'Malley, K. et al. "Constitutively Expressed Rat mRNA Encoding a 70-Kilodalton Heat-Shock-Like Protein," (1985) Molecular and Cellular. Biol. 5(12): 3476-3483.

Ohara, O. et al. "One-Sided Polymerase Chain Reaction: The Amplification of cDNA," (1989) Proc. Natl. Acad. Sci. USA 86: 5673-5677.

Okayama, H. et al. "High-Efficiency Cloning of Full-Length cDNA," (1982) Molecular and Cellular. Biol. 2(2): 161-170.

Okayama, H. et al. "A cDNA Cloning Vector that Permits Expression of cDNA Inserts in Mammalian Cells," (1983) Molecular and Cellular. Biol. 3(2): 280-289.

Palazzolo, M.J. et al. "A Family of Lambda Phage cDNA Cloning Vectors, ?SWAJ, Allowing the Amplification of RNA Sequences," (1987) Gene 52: 197-206.

Polites, H.G. "An Improvement and Simplification in the Gubler-Hoffman Method of cDNA Synthesis," (1988) BioTechniques 6(8): 720-724.

Portela, A. et al. "A Polymer Vector System That Allows Temperature Dependent Gene Amplification and Expression in Mammalian Cells: Regulation of the Influenza Virus NS1 Gene Expression," (1985) Nucleic Acids Res. 13(22): 7959-7977.

Pruitt, S.C. "Expression Vectors Permitting cDNA Cloning and Enrichment for Specific Sequences by Hybridization/Selection," (1988) Gene 66: 121-134.

Putney, S.D. et al. "A New Troponin T and cDNA Clones for 13 Different Muscle Proteins, Found by Shotgun Sequencing," (1983) Nature 302: 718-721.

Rabkin, S.D. et al. "Initiation of cDNA Replication at Cloned Origins of Bacteriophage T7," (1988) J. Mol. Biol. 204: 903-916.

Saiki, R.K. et al. "Primer-Directed Enzymatic Amplification of DNA with a Thermostable DNA Polymerase," (1988) Science 239: 487-491.

Sanger, F. et al. "DNA Sequencing with Chain-Terminating Inhibitors," (1977) Proc. Natl. Acad. Sci. USA 74(12): 5463-5467.

Sargent, T.D. "Isolation of Differentially Expressed Genes," (1987) In Methods in Enzymology vol. 152 Guide to Molecular Cloning, Berger, S.L. et al. eds., Academic Press, Inc., San Diego, pp. 423-432.

Sarkar, G. et al. "RNA Amplification with Transcript Sequencing (RAWTS)," (1988) Nucleic Acids Res, 16(11): 5197.

Sarkar, G. et al. "Access to Messenger RNA Sequence or Its Protein Products Is Not Limited by Tissue or Species Specifically," (1989) Science 244: 331-334.

Sasavage, N.L. et al. "Nucleotide Sequence of Bovine Prolactin Messenger RNA," (1982) J. of Biol. Chem. 257(2): 678-681.

Schowalter, D.B. et al. "The Generation of Radiolabeled DNA and RNA Probes with Polymerase Chain Reaction," (1989) Analytical Biochem. 177: 90-94.

Stoflet, E.S. et al. "Genomic Amplification with Transcript Sequencing," (1988) Science 239: 491-494.

Struhl, K. "Naturally Occuring Poly(dA-dT) Sequences are Upstream Promoter Elements for Constitutive Transcription in Yeast," (1985) Proc. Natl. Acad. Sci. USA 82: 8419-8423.

Studier, F.W. et al. "Use of Bacteriophage T7 RNA Polymerase to Direct Selective High-Level Expression of Cloned Genes," (1986) J. Mol. Biol. 189: 113-130.

Sugimoto, K. et al. "Relative Roles of T7 RNA Polymerase and Gene 4 Primase for the Initiation of T7 Phage DNA Replication In Vivo," (1987) Proc. Natl. Acad. Sci. USA 84: 3977-3981.

Swanstorm, R. et al. "Nucleotide Sequence of Cloned Unintegrated Avian Sarcoma Virus DNA: Viral DNA Contains Direct and Inverted Repeats Similar to Those in Transposable Elements," (1981) Proc. Natl. Acad. Sci. USA 78(1): 124-128.

Tabor, S. et al. "A Bacteriophage T7 RNA Polymerase/Promoter System for Controlled Exclusive Expression of Specific Genes," (1985) Proc. Natl. Acad. Sci. USA 82: 1074-1078.

Tabor, S. et al. "*Escherichia coli* Thioredoxin Confers Processivity on the DNA Polymerase Activity of the Gene 5 Protein Bacteriophage T7," (1987) J. of Biol. Chem. 262(33): 16212-16223.

Tabor, S. et al. "Selective Inactivation of the Exonuclease Activity of Bacteriophage T7 DNA Polymerase by in Vitro Mutagenesis," (1989) J. of Biol. Chem. 264(11): 6447-6458.

Tecott, L.H. et al. "In Situ Transcription: Specific Synthesis of Complementary DNA in Fixed Tissue Sections," (1988) Science 240: 1661-1664.

Tecott. L.H. et al. "Developmental Expression of Proenkephalin mRNA and Peptides in Rat Striatum," (1989) Developmental Brain Res. 49: 75-86.

Thompson, J.D. et al. "Enzymatic Amplification of RNA Purified from Crude Cell Lysate by Reversible Target Capture," (1989) Clin. Chem. 35(9): 1878-1881.

Valentino, K.L. et al. "Distribution of Neuropeptide K-Immunoreactivity in the Rat Central Nervous System," (1986) Peptides 7: 1043-1059.

Volckaert, G. et al. "Molecular Mechanisms of Nucleotide-Sequence Rearrangements in cDNA Clones of Human Fibroblast Interferon mRNA," (1981) Gene 15: 215-223.

Von Sastrow, M. et al. "Ammonium Chloride Alters Secretory Protein Sorting within the Maturing Exocrine Storage Compartment," (1989) J. of Biol. Chem. 264(11): 6566-6571.

Wain-Hobson, S. et al. "Nucleotide Sequence of the AIDS Virus, LAV," (1985) Cell 40: 9-17.

Weier, H-U, et al. "Generation of Labeled RNA Probes from Enzymatically Amplified DNA Templates," (1988) Nucleic Acids Res. 16(24): 11836.

Weiland, J.J. et al. "Infections TYMV RNA from Cloned cDNA: Effects In Vitro and In Vivo of Point Substitutions in the Initiation Codons of Two Extensively Overlapping ORFs," (1989) Nucleic Acids Res. 17(12): 4675-4687.

Wilson, E.M. et al. "Expression Vector pT7: TKII for the Synthesis of Authentic Biologically Active RNA Encoding Vaccinia Virus Thymidine Kinase," (1989) Gene 77: 69-78.

Wu, D.Y. et al. "The Ligation Amplification Reaction (LAR)—Amplification of Specific DNA Sequences Using Sequential Rounds of Template-Dependent Ligation," (1989) Genomics 4: 560-569.

Yool, A.J. et al. "Development of Spontaneous and Glutamate-Evoked Activity Is Altered by Chronic Ethanol in Cultured Cerebellar Purkinje Neurons," (1987) (PubMed Abstract) Brain Res. 420(2): 205-219.

Yool, A.J. et al. "Developmental Changes in K+ Selective Channel Activity During Differentiation of the Purkinje Neuron in Culture," (1988) (PubMed Abstract) J. Neurosci. 8(6): 1971-80.

Zaia, J.A. et al. "Confirmation of HIV Infection Using gene Amplification," (1989) Transfusion Medicine Reviews 3(1 Supp. 1): 27-30.

TEXTBOOK: , Albrets, B. et al. eds. Molecular Biology of the Cell, Second Edition, (1989) Garland Publishing, Inc., New York.

TEXTBOOK: Berger, S.L. et al. eds. Methods in Enzymology vol. 152 Guide to Molecular Cloning, (1987) Academic Press, Inc., San Diego.

TEXTBOOK: Old, R.W. et al. eds. Principles of Gene Manipulation An Introduction to Genetic Engineering, Fourth Edition, (1989) Blackwell Scientific Publications, Oxford.

TEXTBOOK: Sambrook, et al. eds. Molecular Cloning A Laboratory Manual, Second Edition, (1989) Cold Spring Harbor Laboratory Press, USA.

TEXTBOOK: Watson, J.D. et al. eds. Molecular Biology of the Gene, Fourth Edition, vol. I General Principles, (1987) The Benjamin/Cummings Publishing Company, Inc. Menlo Park.

TEXTBOOK: Watson, J.D. et al. eds. Molecular Biology of the Gene, Fourth Edition, vol. II Specialized Aspects, (1987) The Benjamin/Cummings Publishing Company, Inc., Menlo Park.

Augenlicht, L.H. et al, "Cloning and Screening of Sequences Expressed in a Mouse Colon Tumor", (1982) Cancer Research 42: 1088-1093.

Akowitz, Alfred , et al., "A novel cDNA/PCR strategy for efficient cloning of small amounts of undefined RNA", *Gene 81*, (1989),295-306.

Alderson, Ralph F., et al., "Modulation of neuronal choline acetyltransferase activity by factors derived from cultures of non-neuronal cells from the CNS", *Int. J. Devl. Neurosci 7*, (1989),309-322.

Asna, Nitza , et al., "Factor C from rabbit liver", *J. Biol. Chem 264*, (1989),5245-5252.

Belyavskii, A. J., et al., "Amplification of total cDNA in vitro", *Biochemistry 575*, (1988),1498-1501.

Belyavsky, A. , et al., "PCR-based cDNA library construction: general cDNA libraries at the level of a few cells", *Nucl. Acids Res. 17*, (1989),2919-2932.

Berger, Shelby L., et al., "Reverse transcriptase and its associate ribonuclease H: interplay of two enzyme activities controls the yield of single-stranded complementary deoxyribonucleic acid", *Biochemistry 22*, (1983),2365-2372.

Bouvier, Michel , et al., "Two distinct pathways for cAMP-mediated down-regulation of the beta2-adrenergic receptor", *J. Biol. Chem. 264*, (1989),16786-16792.

Brown, Nicholas H., et al., "Functional cDNA libraries from Drosophila embryos", *J. Mol. Biol. 203*, (1988),425-437.

Brysch, Wolfgang , et al., "RNA probes, transcribed from synthesis DNA, for in situ hybridization", *Nucl. Acid Res. 16*, (1988),2333.

Butler, Eugene T., et al., "Bacteriophage SP6-specific RNA polymerase", *J. Biol. Chem 257*, (1982),5772-5778.

\* cited by examiner

MULTI-GENE EXPRESSION PROFILE

RELATED APPLICATIONS

This is a continuation of application Ser. No. 09/286,533, filed Apr. 5, 1999 now U.S. Pat. No. 6,291,170; which is a continuation of application Ser. No. 08/922,965, filed Sep. 3, 1997, now U.S. Pat. No. 5,891,636; which is a continuation of application Ser. No. 08/636,748, filed on Apr. 19, 1996, now U.S. Pat. No. 5,716,785; which is a continuation of application Ser. No. 07/957,647, filed on Oct. 5, 1992, now U.S. Pat. No. 5,545,522; which is a continuation of application Ser. No. 07/411,370, filed on Sep. 23, 1989, now abandoned.

This invention was made with Government support under contract MH23861 awarded by the National Institutes of Health. The Government has certain rights in this invention.

FIELD OF THE INVENTION

The present invention relates generally to the field of recombinant DNA technology and, more particularly, to improved methods for producing amplified heterogeneous populations of RNA from limited quantities of cDNA or other nucleic acids.

BACKGROUND OF THE INVENTION

Selective amplification of cDNA's represents a major research goal of molecular biologists, with particular importance in diagnostic and forensic applications, as well as for general manipulations or genetic materials.

In many important areas of research, such as in studying gene regulation in complex biological systems (e.g., the brain) having multiple phenotypes, obtaining sufficient mRNA for the isolation, cloning, and characterization of specific regulated transcripts is problematic. Research has been hindered by, e.g., the high complexity of the mRNA, the relatively low abundance of many important expressed messages, and the spatially limited expression of these messages. In particular, the identification and cloning of novel regulated messages from discrete cell populations has proven to be a formidable task.

The polymerase chain reaction (PCR) is an extremely powerful technique for amplifying specific nucleic acid sequences, including mRNA in certain circumstances. As described in U.S. Pat. No. 4,683,202 and U.S. Pat. No. 4,683,195 (both of which are incorporated herein by reference), PCR typically comprises treating separate complementary strands of a target nucleic acid with two oligonucleotide primers to form complementary primer extension products on both strands that act as templates for synthesizing copies of the desired nucleic acid sequences. By repeating the separation and synthesis steps in an automated system, essentially exponential duplication of the target sequences can be achieved.

PCR, however, has several well-known imitations. For example, PCR typically requires that terminus and terminus sequence information be known for the synthesis of the primers. Recently, homopolymeric tailing of the 3' terminus (see Frohman, et al., Proc. Natl. Acad. Sci. USA 85: 3998–9002 (1988) and Eberwine et al., Neuroscience Short Course I (Society for Neuroscience) 69–81 (1988)) and the synthesis of highly degenerate nucleotide primers (Gould et al., Proc. Natl. Acad. Sci. USA 86: 1934–1938 (1989)) have been implemented to improve the range of cDNAs that can be cloned with PCR. An additional problem is the low fidelity of the most Widely used enzyme in PCR, *Thermus aquaticus* (Taq) polymerase. This characteristic of Taq results in misincorporations that are propagated through the subsequent cycles of PCR amplification—ultimately producing faulty cDNA libraries. Also, sequences longer than 3 kilobases create difficulties in Taq transcription, which can skew cDNAs to smaller sizes during amplification. Of course, unless modified, PCR provides amplification by DNA replication and not by transcription.

In this regard, Sarkar et al., Science 244: 31–34 (1989), recently described a method, called RAWTS (RNA amplification with transcript sequencing), for detecting extremely low abundance messages in heterologous cell types. This method is a modification of GAWTS (genomic amplification with transcript sequencing see, Stofler, et al., Science 339: 491 (1988)), which incorporates a phage promoter into at least one of the two primers used in PCR. In RAWTS, mRNA is amplified by PCR. A phage promoter incorporated into the PCR oligonucleotide primer allows abundant transcription, from which RNA can be sequenced directly.

Four steps are used in RAWTS: (1) first strand cDNA synthesis from total RNA or mRNA using oligo(dT) or an mRNA-specific oligo primer, dNTPs, and reverse transcriptase; (2) PCR, wherein one or both primers contain a T7 phage promoter attached to a sequence complementary to the region to be amplified; (3) transcription of the cDNA strand with T7 RNA polymerase; and (4) reverse transcriptase-mediated dideoxy sequencing of the resultant mRNA transcript.

In spite of such recent advances, including PCR and its various modifications noted above, there exists a need for improved methods of identifying and cloning mRNAs and of accurate in vitro amplification of selected cDNA's. The methods should produce about 100-fold or more amplification of heterogeneous populations of RNA from limited quantities of cDNA. Preferably, the overall methodologies will be capable of replicating a broad range of messages without prior cloning into vectors and without knowledge of sequence in some instances. The present invention fulfills these and other needs.

SUMMARY OF THE INVENTION

The present invention provides novel processes for amplifying at least one sequence in a collection of nucleic acids sequences, the processes comprising (1) synthesizing a nucleic acid by hybridizing a primer complex to the sequence and extending the primer to form a first strand complementary to the sequence and a second strand complementary to the first strand, wherein the complex comprises a primer complementary to the sequence and a promoter region in anti-sense orientation with respect to the sequence; and (2) transcribing copies of anti-sense RNA off of the second strand. The promoter region, which may be single or double stranded, is capable of inducing transcription from an operably linked DNA sequence in the presence of ribonucleotides and a RNA polymerase under suitable conditions. Suitable promoter regions are prokaryotes, such as from T3 or T7 bacteriophage. The primer is preferably a single stranded nucleotide, of sufficient length to act as a template for synthesis of extension products under suitable conditions and maybe poly(T) or a collection of degenerate sequences.

In another aspect, the invention is directed to a processes for detecting expression of a gene in a preselected cell population comprising steps of:

(a) synthesizing double-stranded cDNA by treating mRNAs from the cell populations with a primer complex comprising an oligonucleotide complementary to one or more of the RNA sequences, the primer linked to a promoter region in an orientation capable of directing transcription of anti-sense RNA;

(b) transcribing the cDNA into anti-sense RNA by introducing an RNA polymerase capable of operably binding to the promoter region; and (c) determining the presence or absence of transcribed anti-sense RNA complementary to mRNA corresponding to the gene.

The cell population may be, e.g., from a human tissue, such as brain nuclei. The cell population may be single cell, or up to 100 to 1,000,000 cells or more as desired.

In another embodiment, the present invention comprises a process for producing a subtractive hybridization probe comprising:

(a) synthesizing a first double-stranded cDNA collection by treating a first mRNA population with a primer complex, wherein the primer is complementary to the RNA sequence and is operably linked to a first promoter region for transcription of the cDNA strand complementary to the primer;

(b) transcribing the first cDNA into anti-sense RNA by introducing a first RNA polymerase capable of binding to the first promoter region;

(c) hybridizing the anti-sense RNA to a second mRNA population, whereby an unhybridized subpopulation of the second RNA population is found;

(d) generating a second double-stranded cDNA collection from the unhybridized subpopulation using a second primer complex comprising a second promoter region in an orientation for transcribing anti-sense RNA complementary to the unhybridized subpopulation; and (e) transcribing the second cDNA into a ribonucleotide probe by introducing a second RNA polymerase capable of binding to the second promoter region.

Additionally, the present invention comprises methods for making cDNA libraries from a collection of mRNA molecules comprising the steps of:

(a) hybridizing one or more primer complexes to a plurality of the mRNA's, wherein each complex comprises an oligonucleotide primer linked to a promoter sequence capable of directing transcription of a DNA sequence complementary to the primer;

(b) producing a collection of double-stranded cDNAs by extending the primers of a plurality of any hybridization duplexes formed between the mRNA's and the complexes wherein each cDNA comprises a first strand complementary to one mRNA molecule and a second strand operably linked to the promoter sequence;

(c) transcribing multiple copies of anti-sense RNA off of the second strand; and (d) preparing a cDNA library from the anti-sense RNA copies.

Importantly, the present invention can be readily provided in kit form for a variety of uses. In addition to instructions, a kit will typically comprise containers of reverse transcriptase, RNA polymerase, and nucleotides which may be labelled, such as with radioactive labels (e.g., $^{14}C$, $^{3}H$, $^{32}P$ and the like).

DETAILED DESCRIPTION OF THE SPECIFIC EMBODIMENTS

Figure 1:
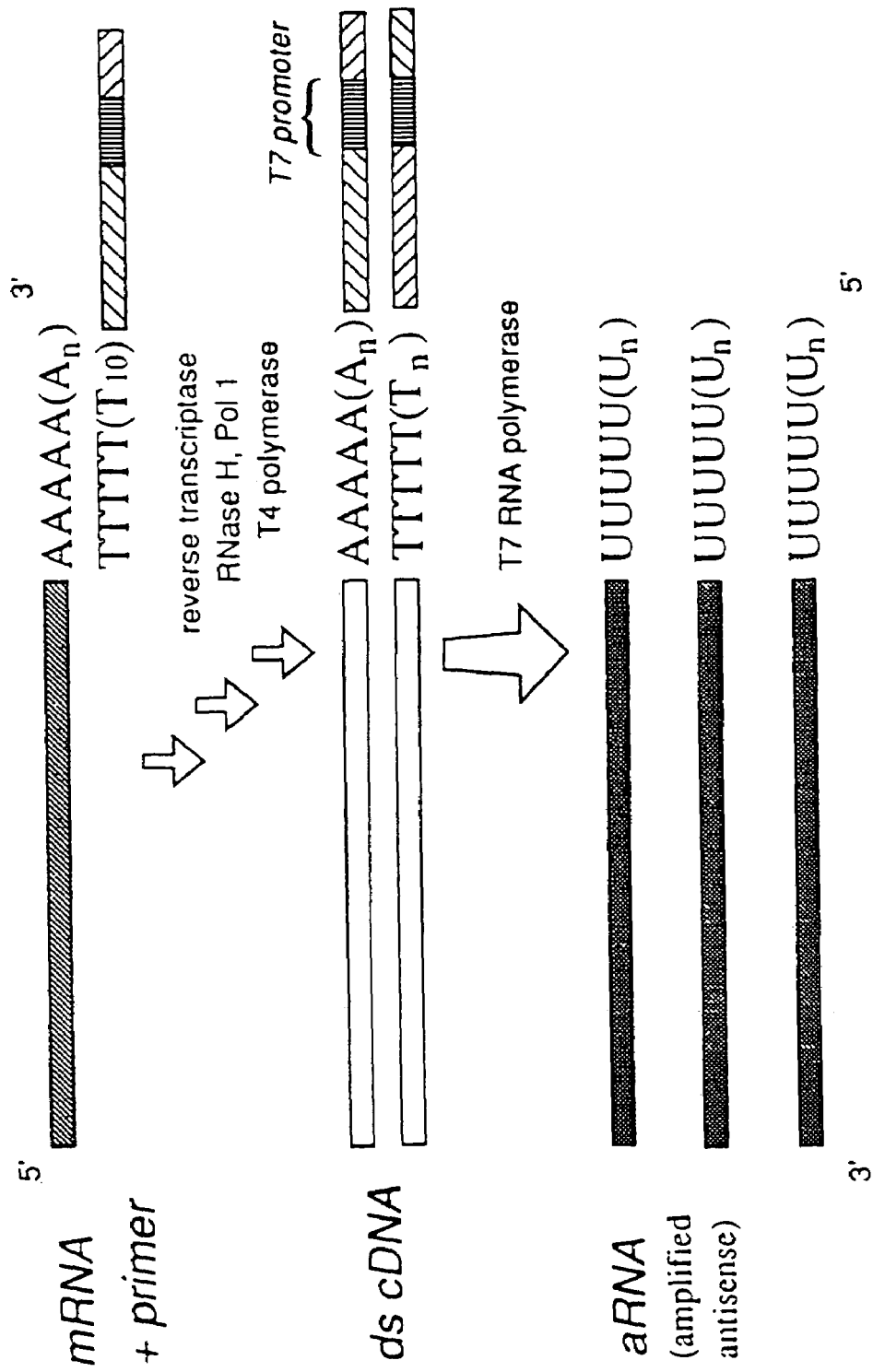
FIG. 1. Paradigm for production of amplified, anti-sense RNA (aRNA). Whole RNA is reverse transcribed using a synthetic primer containing the T7 RNA Polymerase binding site (5' AAA CGA CGG CCA GTG AAT TGT AAT ACG ACT CAC TAT AGG GCG $(T)_{15}$ 3') SEQ ID NO: 1. Second strand cDNA synthesis (producing double-stranded (ds) cDNA) is performed using RNase H and *E. coli* DNA polymerase I (Gubler and Hoffman, Gene 25: 263–269 (1983)). Following blunt-ending of cDNA with T4 DNA polymerase (at which point a functional T7 RNA polymerase promoter is created), the cDNA is purified and transcribed with T7 RNA polymerase, yielding amplified, anti-sense RNA.

In accordance with the present invention, novel methods and compositions are provided for the amplification of broad classes of cDNAs. In typical embodiments, as shown in FIG. 1, these methods involve the incorporation of an RNA polymerase promoter into selected cDNA molecule by priming cDNA synthesis with a primer complex comprising a synthetic oligonucleotide containing the promoter. Following synthesis of double-stranded cDNA, a polymerase generally specific for the promoter is added, and anti-sense RNA is transcribed from the cDNA template. The processive synthesis of multiple RNA molecules from a single cDNA template results in amplified, anti-sense RNA (aRNA) that serves, inter alia, as starting material for cloning procedures using random primers. The amplification, which will typically be at least about 20–40, typically to 50 to 100 or 250-fold, but may be 500 to 1000-fold or more, can be achieved from nanogram quantities or less of cDNA, and is economical, simple to perform under standard molecular biology laboratory conditions (see, Maniatis et al., (1982), *Molecular Cloning: A Laboratory Manual*, Cold Spring Harbor, which is incorporated herein by reference). It is also easily adaptable into kit form.

The techniques of the present invention also provide a number of additional genetic manipulation technologies. The aRNA represents a useful intermediate for construction of complex cDNA libraries from extremely limited amounts of tissue, such as individual brain nuclei, tissue sections, and even single cells. Also, with appropriate amplification primers, aRNA synthesis can be used for the production of specific ribonucleotide probes without prior cDNA cloning into riboprobe vectors. Further, aRNA provides a source of large amounts of single-stranded, anti-sense material for use as driver in subtractive hybridization. For example, two nucleic acid populations, one sense, and one anti-sense, can be allowed to mix together with one population present in molar excess (driver). Sequences present in both populations will form hybrids, whereas sequences present in only one population remain single-stranded (Duguid et al., Proc. Natl. Acad. Sci. USA 85: 5738–5742 (1988)).

In one general embodiment of the present invention, cDNA strands are synthesized from a collection of mRNA's using an oligonucleotide primer complex, i.e., a primer linked to a promoter region. If the target mRNA is the entire mRNA population, then the primer can be a polythymidylate region (e.g., about 5 to 20, preferably about 10 to 15 T residues) which will bind with the poly(A) tail present on the 3' terminus of each mRNA. Alternatively, if only a preselected mRNA is to be amplified, then the primer will be substantially complementary to a section of the chosen mRNA, typically at the 3' terminus. The promoter region is located upstream of the primer at its 5' terminus in an orientation permitting transcription with respect to the mRNA population utilized. This will usually, but not always, mean that the promoter DNA sequence operably linked to the primer is the complement to the functional promoter sequence. When the second cDNA strand is synthesized, the promoter sequence will be in correct orientation in that strand to initiate RNA synthesis using that second cDNA strand as a template. Preferably, the promoter region is derived from a prokaryote, and more preferably from the group consisting of SP6, T3 and T7 phages (Chamberlin and Ryan, in *The Enzymes*, ed. P. Boyer (Academic Press, New York) pp. 87–108 (1982), which is incorporated herein by reference). A preferred promoter region is the sequence from the T7 phage that corresponds to its RNA polymerase binding site (5' AAA CGA CGG CCA GTG AAT TGT AAT ACG ACT CAC TAT AGG GCG 3'SEQ ID NO: 2.

Once the oligonucleotide primer and linked promoter region hybridize to the mRNA, a first cDNA strand is synthesized. This first strand of cDNA is preferably produced through the process of reverse transcription, wherein DNA is made from RNA, utilizing reverse transcriptase following standard techniques. This enzyme, present in all retroviruses (e.g., avian myeloblastoma virus), adds deoxyribonucleotides to the 3' terminus of the primer (Varmus, Science 240: 1427–1435 (1988)).

The second strand cDNA, creating double-stranded (ds) cDNA, can be synthesized by a variety of means, but preferably with the addition of RNase H and *E. coli* DNA polymerase. RNase assists breaking the RNA/first strand cDNA hybrid, and DNA polymerase synthesizes a complementary DNA strand from the template DNA strand. The second strand is generated as deoxynucleotides are added to the 3' terminus of the growing strand. As the growing strand reaches the 5' terminus of the first strand DNA, the complementary promoter region of the first strand will be copied into the double stranded promoter sequence in the desired orientation.

Thereafter, cDNA is transcribed into anti-sense RNA (aRNA) by introducing an RNA polymerase capable of binding to the promoter region. The second strand of cDNA is transcribed into aRNA, which is the complement of the initial mRNA population. Amplification occurs because the polymerase repeatedly recycles on the template (i.e., reinitiates transcription from the promoter region). Importantly, this particular technique thus enables replicating a broad range of cDNA's without prior cloning into vectors. Recycling of the polymerase on the same template avoids propagation of errors.

The RNA polymerase used for the transcription must be capable of operably binding to the particular promoter region employed in the primer complex. A preferred RNA polymerase is that found in bacteriophages, in particular T3 and T7 phages. Substantially any polymerase/promoter combination can be used, however, provided the polymerase has specificity for that promoter in vitro sufficient to initiate transcription.

The most preferred polymerase is T7 RNA polymerase. The extremely high degree of specificity shown by T7 RNA polymerase for its promoter site (Chamberlin et al., in *The Enzymes*, ed. P. Boyer (Academic Press, New York) pp. 87–108 (1982)) has previously made this enzyme a useful reagent in a variety of recombinant DNA techniques, including in vitro RNA synthesis from plasmids containing the promoter site for use as probes (Melton et al., Nucl. Acids Res., 12: 7035–7056 (1984)), for in vitro translation studies (Krieg et al., Nuc. Acids Res. 12: 7057–7070 (1984)), and for use in producing synthetic oligoribonucleotides (Milligan et al., Nuc. Acids Res. 15: 8783–8798 (1987)). The natural T7 promoters share a highly conserved sequence covering about bp −17 to about +6 relative to the start of the RNA chain (Dunn and Studier, J. Mol. Biol. 166: 477–535 (1983) and J. Mol. Biol. 175: 111–112 (1984), both of which are incorporated herein by reference). The lack of efficient termination signals for T7 polymerase also enable it to make transcripts from almost any DNA (see, Rosenberg et al., Gene 56: 125–135 (1987), which is incorporated herein by reference). The T7 polymerase is also available from a number of commercial sources, such as Promega Biotech, Madison, Wis., and in a concentrated form (1000 units/µl) from Epicenter Technologies, Madison, Wis. Other suitable polymerases include, by way of example and not limitation: T3 or SP6 (Promega) RNA polymerase and *E. coli* RNA polymerase, and will vary in accordance with the promoter region(s) utilized.

Depending on the ultimate use of the aRNA, included in the transcription reaction mixture will be the necessary nucleotide triphosphates, where one or more of the nucleotides may be labeled, particularly with a radioactive label, such as $^{32}S$, $^{32}P$, $^{3}H$, or the like. Alternatively, nucleotides may be obtained which are labeled with biotin, where these nucleotides will become incorporated in the aRNA (see, Sive and St. John, Nucl. Acids Res. 16: 10937 (1988) and Duguid et al., Proc. Natl. Acad. Sci. USA 85: 5738–5742 (1988) both of which are incorporated herein by reference). The biotin may then be used for binding to avidin, which is labeled with an appropriate label capable of providing for detection. A wide variety of labelling techniques are well known to those skilled in the art and may be used in accordance with standard procedures (see, U.S. Pat. No. 4,755,619, which is incorporated herein by reference).

In general, when characterizing the aRNA transcripts, various well known procedures may be employed. The transcripts may be removed from the reaction mixture and separated on an appropriate gel. The aRNA may be used as template for cDNA synthesis and subjected to PCR to further expand desired sequences. The aRNA may be used unmodified for further cloning, expression, use as probe or driver nucleic acid in subtractive hybridization, in Cot or Rot analysis, or the like.

Essentially any nucleic acid sequence, in purified or nonpurified form, can be utilized as the starting nucleic acid(s) for the methods of the present invention, provided it contains or is suspected to contain the specific nucleic acid sequence desired (i.e., complementary to the primer). It is only generally preferred that a sufficient number of bases at one end of the sequence be known in sufficient detail so that a primer template can be prepared which will hybridize to one of the strands of the desired sequence. A mixture of any of these nucleic acids may also be employed (including specific or degenerate sequences, see, e.g., PCR U.S. patents), or the nucleic acid produced from a previous amplification reaction using the same or different primers may be utilized. The specific nucleic acid sequence to be amplified may be only a fraction of a larger molecule or can be present initially as a discrete molecule, so that the specific sequence constitutes the entire nucleic acid.

It is also not necessary that the sequence to be amplified be present initially in a pure form; it may be a minor fraction of a complex mixture, or a portion of a nucleic acid sequence, the existence of which is due to a particular microorganism's presence. The starting nucleic acid sequence may contain more than one desired specific nucleic acid sequence, each of which may be the same or different from each other. Therefore, the amplification process is useful not only for producing large amounts of one specific nucleic acid sequence, but also for amplifying simultaneously more than one different specific nucleic acid sequence located on the same or different nucleic acid molecules.

The nucleic acid(s) may be obtained from any source, for example, from plasmids such as pBR322, from cloned DNA or RNA, or from natural DNA or RNA from any source, including bacteria, yeast, viruses, organelles, and higher organisms such as plants or animals. DNA or RNA may be extracted from blood, tissue material or cells by a variety of techniques such as those described by Maniatis et al., supra.

As used herein, the term "primer complex" refers to an oligonucleotide having two components: (1) a primer that may be synthetic or a purified restriction digest and (2) a specifically oriented RNA polymerase promoter region. The primer component will be capable of acting as a point of initiation of synthesis, typically DNA replication, when placed under conditions in which synthesis of a primer extension product that is complementary to a nucleic acid strand is induced, i.e., in the presence of appropriate nucleotides and a replicating agent (e.g., a DNA polymerase) under suitable conditions, which are well known in the art.

The primer is preferably a single stranded oligodeoxynucleotide. The primer must be sufficiently long to act as a template for the synthesis of extension products in the presence of the replicating agent. The exact lengths of the primers and the quantities used will depend on many factors, including temperature, degree of homology and other conditions. For example, when amplifying a specific sequence, the oligonucleotide primer typically contains between about 10 and 50 nucleotides, preferably 15–25 or more nucleotides, although it may contain fewer nucleotides, depending, e.g., on the promoter sequence. For other applications, the oligonucleotide primer is typically, but not necessarily, shorter, e.g., 7–15 nucleotides. Such short primer molecules generally require cooler temperatures to form sufficiently stable hybrid complexes with template.

The oligonucleotide primers may be prepared using any suitable method, such as, for example, the well known phosphotriester and phosphodiester methods, or automated embodiments thereof. In one such automated embodiment, diethylphosphoramidites are used as starting materials and may be synthesized as described by Beaucage et al., Tetrahedron Letters 22: 1359–1962 (1981). One method for synthesizing oligonucleotides on a modified solid support is described in U.S. Pat. No. 4,458,066. It is also possible to use a primer which has been isolated from a biological source (such as a restriction endonuclease digest).

The primers herein are selected to be "substantially" complementary to the different strands of each specific sequence to be amplified, i.e., the primers should be sufficiently complementary to hybridize with their respective strands. Therefore, the primer sequence need not reflect the exact sequence of the template, and can, in fact, be "degenerate." Non-complementary bases or longer sequences can be interspersed into the primer, provided that the primer sequence has sufficient complementarity with the sequence of the strand to be amplified to permit hybridization and extension.

Generally, it is not necessary to know the sequences of a target mRNA, as the primer may be a poly(T) of sufficient length to hybridize with substantially an entire population of messages (i.e., poly(T)$_n$, wherein n is typically from about 5 to 50 or more). Of course, when more sequence knowledge is available for a target RNA, the primer may be designed more specifically, which greatly increases the efficiency of the amplification. Moreover, the primer may actually comprise a collection of primer sequences, such as where more than one target sequence exists. Also, if there is ambiguity in the sequence information, a number of primers should be prepared. In particular, when any of several possible nucleic acid sequences encoding a protein could be correct based on polypeptide sequence obtained from a fragment of the protein, a collection of primers containing sequences representing most or all of the possible codon variations (utilizing codon degeneracy) can be prepared.

Similarly, the promoter region will be capable of initiating transcription of an operably linked DNA sequence in the presence of ribonucleotides and an RNA polymerase under suitable conditions. The primer and promoter components will be linked in an orientation to permit transcription of a DNA strand that is complementary to the primer, i.e., the aRNA transcription will generally be in the same direction as the primer extension. A linker oligonucleotide between the components, if present, will typically comprise between about 5 and 20 bases, but may be smaller or larger as desired.

The second component of the primer complex, the promoter region, may be single stranded or double stranded. The region will usually comprise between about 15 and 250 nucleotides, preferably between about 25 and 60 nucleotides, from a naturally occurring RNA polymerase promoter or a consensus promoter region (Alberts et al., in *Molecular Bioloqy of the Cell*, 2d Ed., Garland, N.Y. (1989), which is incorporated herein by reference). In general, prokaryotic promoters are preferred over eukaryotic promoters, and phage or virus promoters most preferred. As used herein, the term "operably linked" refers to a functional linkage between the affecting sequence (typically a promoter) and the controlled sequence.

Promoter sequences are regions where RNA polymerse bind tightly to the DNA and contain the start site and signal for RNA synthesis to begin. In *E. coli*, typically the RNA polymerase molecules covers about 60 nucleotides when it binds to the DNA. Native strong promoters typically contain two highly conserved DNA sequences, each about six nucleotides long, which are located upstream from the start site and separated from each other by about 17 nucleotides of unrecognized DNA. When promoters are compared, the regions of similarity are termed "consensus" sequences.

A wide variety of promoters and polymerases showing specificity for its cognate promoter are known. For example, the *Bacillus subtilis* phage SPO1 synthesizes two or three new σ factors which, when combined with host RNA polymerase, recognize only SPO1 promoters. Probably the best studied phage promoter/polymerase system is *E. coli* phage T7. T7 makes an entirely new polymerase that is highly specific for the 17 late T7 promoters. Rather than having two separate highly conserved regions like *E. coli* promoters, the late T7 promoters have a single highly conserved sequence from −17 to +6 relative to the RNA start site. The *Salmonella* phage SP6 is very similar to T7. The simplicity of the T3, T7, and SP6 systems have made them especially amendable to the expression of heterologous DNA in genetic engineering applications.

At least one example is known of an RNA polymerase which recognizes a single-stranded promoter. *E. coli* phage N4 makes an RNA polymerase which recognizes early N4 promoters on native single stranded N4 DNA. For a detailed description of promoters and RNA synthesis upon DNA templates, see Watson et al., *Molecular Biology of The Gene*, 4th Ed., Chapters 13–15, Benjamin/Cummings Publishing Co., Menlo Park, Calif., which is incorporated herein by reference.

As used herein the term "anti-sense orientation" means that the promoter will initiate transcription of the complementary sequence to the target sequence (for example, when mRNA is the target sequence of the primer, anti-sense RNA will be produced).

The high specificity of bacterial phage RNA polymerases for their cognate promoters, in particular, provides a novel subtractive hybridization paradigm, although other polymerase and promoters may be used. Because aRNA is anti-sense with respect to the input RNA, aRNA produced from RNA population #1 (using cDNA synthesized with, e.g., the T7 promoter-containing primer and T7 RNA polymerase) can be hybridized with RNA population #2. Unhybridized poly(A)+ RNA is then be transcribed into cDNA using reverse transcriptase and a primer containing a different RNA polymerase promoter (such as T3 or SP6). Following second strand synthesis, these cDNAs are then be amplified with the addition of the appropriate RNA polymerase, yielding a high specific activity probe which is used to screen an appropriate cDNA or genomic library. Such a technique has an advantage over most other subtractive hybridization protocols in that physical separation of single and double stranded material is not required to generate the subtractive probe; additionally, the resultant aRNA can be radioactively labeled in excess of $1\times10^9$ cpm/µg (see, Melton, supra), permitting screening of a large number of clones with a limited amount of subtractive material.

Although the aRNA paradigms of the present invention will provide a useful adjunct to PCR in a wide variety of diagnostic or other studies, especially facilitated are studies of gene expression in essentially any mammalian cell or cell population. Although the cell may be from blood (e.g., white cells, such as T or B cells) a typical source of cell or tissue will be solid organs, such as brain, spleen, bone, heart, vascular, lung, kidney, liver, pituitary, endocrine glands, lymph node, dispersed primary cells, tumor cells, or the like. Thus, in the neural research area, identification of mRNAs which vary as a function of arousal state, behavior, drug treatment, and development, for example, has been hindered by both the difficulty in construction of cDNA libraries from small brain nuclei and in the relative spatial insensitivity of subtractive hybridization techniques. Use of the aRNA amplification method in construction of cDNA libraries from individual brain nuclei will provide for greater representation of low-abundance mRNAs from these tissues compared with their representation in whole brain cDNA libraries, and facilitate cloning of important low-abundance messages.

The RNA amplification technology can also be applied to improve methods of detecting and isolating nucleic acid sequences that vary in abundance among different populations, such as in comparing mRNA expression among different tissues or within the same tissue according to physiologic state. Methods for examining differential expression typically involve subtractive hybridization, wherein two nucleic acid populations, one sense and one anti-sense, are allowed to mix with one another. One population is present in molar excess ("driver") such that sequences represented in both populations form hybrids, whereas sequences present in only one population remain single-stranded. Thereafter, various well known techniques are used to separate the unhybridized molecules representing differentially expressed sequences.

Most methods of subtractive hybridization require that large amounts (generally tens of micrograms) of nucleic acid be available for use as "driver" in such experiments. This limits usefulness in examining differential expression of mRNAs present in a biological material that is available in small supply. This is overcome by cloning the nucleic acid populations of interest prior to subtraction, so that the cloning vector is used to amplify the amount of nucleic acid available for hybridization. However, because subtraction requires previous cloning, it is complicated, suffers from under- and over-representation of sequences depending on differences in growth rates in the mixed population, and may risk recombination among sequences during propagation of the mixed population. The aRNA technology of the present invention circumvents these problems by allowing production of large amounts of anti-sense RNA from limited amounts of nucleic acid, without the need for previous cloning. PCR produces both sense- and anti-sense strands, so is less favorable for this use.

An additional embodiment of the present invention is "differential amplification". This procedure allows amplification of only differentially expressed sequences by virtue of the specificity among prokaryotic RNA polymerase promoters.

Also, the novel aRNA technology is used to identify sequences of interest from small amounts of nucleic acid by detecting the amplified sequences in the aRNA product. The aRNA amplification is uniform among individual sequences, and thus, it is useful in estimating relative levels of representation of a given sequence relative to other sequences within a population. Such quantitative resolution finds use in molecular diagnostics (such as in diagnosing thalassemias characterized by abnormal levels of hemoglobin gene expression), where diagnosis can rest not on absolute presence or absence of a sequence, but on whether a given sequence is present at abnormally high or low levels relative to other sequences. By providing relatively linear amplification, the present invention offers advantages to PCR.

Anti-sense RNA has a wide variety of uses in both analytical research and therapeutics. Anti-sense RNA functions in several prokaryotic systems to regulate gene expression. Similarly, anti-sense RNA can regulate the expression of many eukaryotic genes. This permits blocking expression of undesirable genes. Therapeutic use of anti-sense RNA therefore involves in vitro synthesis of anti-sense RNA with subsequent introduction into the subject (see, generally, Melton, *Antisense RNA and DNA*, Cold Spring Harbor (1988), which is incorporated herein by reference).

Another application of the inventive aRNA technology is in detection of variant regions flanking a common sequence, such as for molecular diagnostics. By designing an amplification primer that recognizes a commonly shared sequence, aRNA is produced that contains not only the common region recognized by the primer, but also 5'-flanking sequence useful in detecting sequence variants. An advantage over PCR is that only one region of shared sequence need be known; PCR generally requires that shared sequences be known both 5'- and 3'- to the region of interest, and that these flanking regions be sufficiently close to allow efficient amplification. Thus, for example, aRNA can be produced from limited amounts of clinical material to allow pathogen-specific sequences (such as those distinguishing viral types) to be identified, genetic polymorphisms to be detected, or alternate splicing variants to be characterized, all in accordance with standard techniques.

The materials for use in the methods of the present invention are ideally suited for preparation of kits produced in accordance with well known procedures. Such a kit may comprise containers, each with one or more of the various reagents (typically in concentrated form) utilized in the methods, including, for example, buffers, the appropriate nucleotide triphosphates (e.g., dATP, dCTP, dGTP and dTTP; or rATP, rCTP, rGTP and UTP), reverse transcriptase, DNA polymerase, RNA polymerase, and one or more primer complexes of the present invention (e.g., appropriate length poly(T) or random primers linked to a promoter reactive with the RNA polymerase). A set of instructions will also typically be included.

The following experimental examples are offered by way of illustration and not by way of limitation.

EXPERIMENTAL

Materials

Avian myeloblastoma reverse transcriptase was obtained from Seikagaiku, St. Petersburg, Florida; RNase H, DNA polymerase I, T4 DNA polymerase, and all restriction enzymes were from Bethesda Research Laboratories, Bethesda, Md.; S1 nuclease was from Boehringer Mannheim, West Germany; RNase Block and T3 RNA polymerase were obtained from Stratagene, La Jolla, Calif.; T7 RNA polymerase (80 units/µl) was obtained from Promega, Madison, Wis.; and radioactive nucleotide triphosphates were from Amersham, Arlington Heights, Ill. Oligonucleotides were synthesized on a BioSearch Model 8600 synthesizer and were purified by acrylamide gel electrophoresis prior to use. The rat β-actin clone in the pCD vector was isolated by hybridization to the published sequence (Nudel et al., Nuc. Acids Res. 11: 1756–1771 (1983)). pGEM-2 plasmids containing alpha subunit sequences of $G_s$, $G_o$, $G_{i1}$, $G_{i2}$, $G_{i3}$ were prepared according to Jones et al., J. Biol. Chem. 262: 1421–14249 (1987). IB15 cDNA (cyclophilin) cloned into the pCD vector was prepared according to Sutcliffe et al., Cold Spring Harbor Symposia on Quantitative Biology 48: 477–484 (1983).

cDNA Synthesis

Total RNA was extracted from whole rat cerebellum by guanidium thiocyanate extraction followed by cesium chloride gradient ultracentrifugation (Chirgwin et al., Biochemistry 24: 5294–5299 (1987)). 40 µg of total RNA was primed with 100 ng of primer (5' AAA CGA CGG CCA GTG AAT TGT AAT ACG ACT CAC TAT AGG CGC (T)$_{15}$ 3') SEQ ID NO:1 as schematized in FIG. 1. The RNA/primer mix was subjected to three cycles of heat denaturation at 80° C. alternating with incubation on ice for 3 minutes each. First strand synthesis was performed with avian myeloblastoma virus reverse transcriptase, and second strand cDNA was synthesized using RNase H and E. coli DNA polymerase I (Gubler et al., Gene 25: 263–269 (1983)). cDNA was made blunt ended by treatment with 2 units T4 DNA polymerase for 15 minutes at 37° C. Unincorporated triphosphates were removed by drop dialysis against double-distilled H$_2$O for 2 hours, using a 0.025 mm nitrocellulose filter (Millipore, Bedford, Mass.). Identical reactions were performed for each synthesis with and without incorporation of 30 uCI of 400 Ci/mM α-$^{32}$P dCTP.

aRNA Synthesis 3 ng of cDNA was amplified in each Reaction. Reactions conditions were: 40 mM Tris pH 7.5, 6 mM MgCl$_2$, 10 mM NaCl, 2 mM spermidine, 10 mM DTT, 500 µM each ATP, GTP, and UTP, 12.5 µM CTP, 30 uCI α-$^{32}$P-CTP (3000 Ci/mM). 10 units RNase Block, and 80 units T7 RNA polymerase in a volume of 20 µl. Reactions were carried out for 2 hours at 37° C. Incorporated radioactivity was determined by TCA precipitation and scintillation counting of Cerenkov radiation (Maniatis et al., supra).

In Situ Transcription (IST) and Amplifications

Fresh frozen cerebellar tissue was cut by cryostat in a horizonal plane into 11 µm thick sections and processed for in situ transcription (IST) as previously described (Tecott et al., Science 240: 1661–1664 (1988)). Oligonucleotide hybridization proceeded for 12 hours followed by washing for 5 hours in 0.5×SSC at room temperature. The IST reaction conditions were the same as described in Eberwine et al., Neuroscience Short Course I (Society for Neuroscience) 69–81 (1988), with the autoradiographic signals generated using a ratio of 250 nM $^{32}$P dCTP/2.5 uM dCTP in the reaction. The cDNA used in amplifications was synthesized by IST using 250 uM each of dATP, dGTP, TTP and dCTP. After the IST, cDNA transcripts were isolated (Tecott et al., Science 240: 1661–1664 (1988)), and second strand cDNA was synthesized as described (Maniatis et al., supra). The hairpin-loop structure was removed by S1-nuclease treatment for 5 minutes. Subsequently the cDNA was blunt-ended using T4 DNA polymerase. After phenol/chloroform extraction and ethanol precipitation with 5 micrograms of carrier tRNA, cDNA was dissolved in 10 microliters of H 20 and drop dialyzed for 4 hours against H$_2$O. The cDNA was removed and 2 uL was used for each aRNA amplification. Amplifications were performed as previously described with the exception that the concentration of non-labeled CTP in the reaction was 1.25 uM rather than 12.5 uM.

Single Cell Infections and Amplifications

Primary cultures of cerebellar neurons were established from rat embryos at gestation day 20, using techniques described in Gruol et al., J. Neurosci. 7: 1271–1293 (1987). Cultures consisting of Purkinje neurons, cerebellar interneurons, and glia were grown on polylysine in modified Eagles medium with 10% added serum. Identified mature Purkinje cells at 21 days in vitro were selected for cDNA synthesis. The whole-cell patch clamp recording technique (Yool et al., J. Neurosci. 8: 1971–1980 (1988)) was used to introduce the components for first strand synthesis intracellularly, while continuously monitoring cell physiology. Polished, uncoated patch electrodes (3–5 MOhm) were filled with 8–10 µl of the reaction mix, consisting of buffered saline (154 mM KCl, 6 mM NaCl, 5 mM MgCl$_2$, 0.1 µM CaCl$_2$, 10 mM Hepes pH 7.3), reverse transcriptase (2 units/µl), T7$_{55}$ oligonucleotide primer (0.5 ng/µl), and 1 mM each of dATP, dCTP, dGTP, TTP. The duration of loading and incubation in the whole-cell recording configuration ranged from 5–20 min. Simultaneous monitoring of electrical properties of the cell (sustained spontaneous firing, resting membrane potential near −60 mV, and input resistance>100 MOhm) indicated the loading process did not impair functions that are sensitive to damage.

The soma of each cell was harvested after loading with suction applied through the electrode holder after opening the electrode tip by gently touching it against the culture plate. Separate electrodes were used for each cell. Harvested soma were incubated individually in the electrodes for 1 hr at 37° C. to facilitate first strand synthesis, then ejected from the electrodes into EDTA (10 mM) in two volumes of ethanol, and frozen on dry ice. The samples were processed by addition of 5 µg of tRNA and NaCl to a final concentration of 500 mM and centrifuged to precipitate the nucleic acids. Residual cellular protein was removed by phenol/chloroform extraction and the nucleic acid concentrated and further purified by two ethanol precipitations. The nucleic acid was dissolved in 25 µl of H 20 and heated at 95° C. for 3 minutes followed by quick cooling on ice to separate the cDNA from RNA. To make second-strand cDNA, the volume was increased to 50 µl with 2× concentrated DNA polymerase buffer (Maniatis et al., supra) and incubated with 10 units of DNA polymerase at 37° C. for 60 minutes. This mixture was phenol/chloroform extracted followed by two ethanol precipitations. The DNA was treated with 1 unit of S1 nuclease for 5 minutes (Maniatis et al., supra) to remove the hairpin-loop structure and the sample was phenol/chloroform extracted and ethanol precipitated. The ends of the DNA were blunt-ended by incubation of the DNA with 5 units of T4 DNA polymerase and 200 µM each of the deoxynucleotide triphosphates (Maniatis et al., supra) at 37° C. for 15 minutes followed by phenol/chloroform extraction and ether extraction. This DNA mixture was drop dialyzed against 50 ml of $H_2O$ for 4 hours. The DNA was then concentrated to 10 µl under vacuum. Between 3 and 5 µl of this material was used in each amplification reaction. aRNA amplification was done essentially as described above with the exception that nonlabeled dCTP was used at a final concentration of 1.25 µM and, when using 3 µl of DNA template, the amount of $^{32}P$-labeled dCTP was increased to 50 uCi.

Northern and Southern Analyses

Swiss-Webster mouse and Sprague-Dawley rat genomic DNA were isolated as described (Maniatis et al., supra). 20 µg of each species DNA was digested overnight with 20 units of the following enzymes: BamHI, EcoRI, PstI. The DNA was electrophoresed on a 1% agarose gel and blotted to nitrocellulose (Maniatis et al., supra). pCD-actin was restriction enzyme digested with 10 units PvuII. $G_s$, $G_o$, $G_{i1}$, $G_{i2}$, and $G_{i3}$ containing plasmids were digested with restriction enzymes as follows: $G_s$: EcoRI and BamHI; $G_o$: EcoRI and EcoRV; $G_{i1}$: EcoRI and XbaI; $G_{i2}$: EcoRI and Sau96; and $G_{i3}$: EcoRI and EcoRV. These restriction enzyme digestions yield DNA fragments that have been used as specific probes for individual G protein alpha subunits (Jones et al., J. Biol. Chem. 262: 14241–14249 (1987)). pCD-IB15 was digested with BamHI (Sutcliffe et al., supra). Restriction digested plasmids (10 µG each for all G-protein plasmids and actin, and 5 ug for IB15) were electrophoresed on a 1% agarose gel and transferred to nitrocellulose as for the genomic DNA. Northern blots of whole mouse brain and rat cerebellar RNA (15 µG each) were made by blotting 1.2% agarose/3% formaldehyde gels to nitrocellulose in 20×SSC buffer (Maniatis et al., supra). Size standards (1.4 kb and 0.7 kb) for Northern blots were provided by the in vitro transcription of linearized positive control pGEM-2 plasmid with T7 RNA polymerase. Southern and Northern transfers were pre-hybridized overnight at 42° C. in: 50% formamide, 6×SSC, 5× Denhardt's solution, and 100 µg/µl sheared, autoclaved salmon sperm DNA. For hybridization, $2.5 \times 10^6$ cpm of aRNA was added to the bag and incubated in the same buffer for 48 hours at 42° C. Blots were washed in 0.1×SSC/0.2% SDS for 1 hour at 42° C. and exposed to Kodak XAR film at −80° C. with CRONEX® x-ray intensifying screen (DuPont, Wilmington, Del.) for suitable time periods.

General Characteristics of aRNA Amplification

For the general characteristics of aRNA amplification, see, Melton et al., Nuc. Acids Res. 12: 7035–7056 (1984), which is incorporated herein by reference, which utilized in vitro transcription from plasmid vectors using SP6 RNA polymerase. The degree of amplification obtained was strongly dependent on the enzyme concentration and incubation time. Using the same amount of template (3 ng) and varying the amount of T7 RNA polymerase from 10 units to 80 units provided a 4-fold improvement in yield of aRNA. Maximum levels of amplification were obtained from incubation times between 2 and 4 hours; for incubations longer than 4 hours, TCA precipitable radioactivity began to decrease. In optimizing the reaction, it was found that increased UTP concentration (to 1 mM) during amplification increases aRNA synthesis, while inclusion of glycogen (used as a nonspecific carrier during cDNA precipitation) inhibits the aRNA reaction. Additionally, excess primer acts as an inhibitor of the reaction.

In order to assess the role of additional sequence located 5' to the T7 promoter site in aRNA production (potentially necessary to stabilize the enzyme-DNA interaction), amplifications were performed with synthetic primer lengths of 38, 57, and 80 nt, identical except for additional 5' sequence derived from Bluescript plasmid. Although cDNA generated from all three primers amplified equally well, the 57 nt primer (termed $T7_{57}$) SEQ ID NO: 1 gave the best yield of cDNA and was used for all subsequent amplification reactions. Additionally, cDNA primed with a T3 RNA polymerase promoter site (55 nucleotides long containing a 3' poly dT tract of 15 bases) was amplified with T3 RNA polymerase. This promoter-polymerase combination also generates a similar size distribution of amplified material, but yields approximately 75% of TCA-precipitable radioactivity as compared to equal units of T7 RNA polymerase. Using cDNA synthesized from total cerebellar RNA with the $T7_{57}$ primer, an 80-fold molar amplification was achieved as measured by TCA-precipitable radioactivity.

Amplification of a Broad Range of mRNA Sequences from Total Cerebellar RNA

Because the 51 promoter sequence is specific for T7 RNA polymerase (Chamberlin et al., J. Biol. Chem. 248: 2235–2244 (1973) and Chamberlin et al., in The Enzymes, ed. P. Boyer (Academic Press, New York) pp. 87–108 (1982)) and the RNA polymerase is capable of producing transcripts of 7 kb or larger (Melton et al., supra), it was expected that the aRNA produced would represent accurately the size and complexity of the synthesized cDNA. To test this, cDNA was synthesized from total cerebellar RNA using the $T7_{57}$ primer. A nonlabeled portion of this cDNA was then amplified with T7 RNA polymerase in the presence of $\alpha$-$^{32}P$ CTP. The size distribution of cDNA and aRNA were very similar.

To characterize further the aRNA produced, Southern blot analysis of mouse and rat genomic DNA were performed using labeled aRNA derived from rat cerebellum as a probe. The aRNA hybridized to a broad distribution of sequences, indicating considerable sequence heterogeneity in the amplified material. Additionally, the aRNA showed marked sequence specificity for rat genomic DNA over that of mouse. A similar experiment was performed using aRNA to probe a Northern blot of whole rat cerebellar RNA. Again, the aRNA bound to a wide range of sequences indicating sequence heterogeneity in the amplified material. Approximately 30% of the total grain density of the bound material was found in the 18S and 28S ribosome bands. This is consistent with the yield of cDNA corresponding to these RNA species when cDNA is made from total RNA, suggesting that aRNA abundance is representative of the parent cDNA.

In order to quantify the complexity of amplified material, $R_ot$ hybridization analysis (Van Ness et al., Nuc. Acids Res. 10: 8061–8077 (1982)) of the aRNA was performed. Although a variety of hybridization and RNase conditions were tested, it was not possible to adequately reduce the non-hybridized background of the aRNA; 40% of total single-stranded aRNA remained TCA-precipitable after 500 µg/ml RNase A treatment in 0.5M NaCl at 37° C. for 30 minutes. This material was fully digested following sample boiling. Thus, the heterogeneous amplified material has considerable secondary and tertiary structure.

Detection of Specific Sequences in aRNA Synthesized from Nanogram Quantities of cDNA In order to be useful in the detection and characterization of regulated transcripts, an amplification method must be able to amplify low-abundance transcripts. To detect such transcripts, aRNA was generated from 3 ng of cerebellar cDNA which had been primed with the $T7_{57}$ primer. The aRNA was labeled to a specific activity of $5 \times 10^8$ cpm/µg. $2.5 \times 10^6$ cpm were used to probe 10 µg each of plasmids containing inserts for rat actin, and the alpha subunits of rat G-proteins $G_s$, $G_o$, $G_{i1}$, $G_{i2}$, and $G_{i3}$. The vector sequences in each lane serve as an internal non-specific hybridization control. Following washing of filters in 0.1×SSC/0.1% SDS at 42° C., strong signals were visible in the actin and $G_s$ lanes. Other G protein mRNAs were not visible using this exposure time; however, since the $G_i$ and $G_o$-protein alpha subunits share considerable homology, this may be due to dilution of the aRNA for these G-protein alpha subunits among the multiple DNA restriction fragments encoding these sequences. In order to test this possibility, the presence of particular messages in the aRNA was assayed by probing slot-blots of aRNA and parent cDNA with random hexamer-primed probes for actin and the G-proteins. Qualitatively identical results were found for both cDNA and aRNA: a very strong signal was discerned for the actin probe in both aRNA and cDNA, a weaker signal was observed for $G_s$, and very weak signals were discerned for $G_o$, $G_{i1}$, and $G_{i3}$.

Detection of Specific aRNA Transcripts from Cerebellar Tissue Sections

The determined IST autoradiographic signal suggested that cDNA synthesis occurred in many cell types, with high signal density in the granule cell layer of the cerebellum. This result reflects the expected increase in amount of A+-mRNA in regions of high cellular density. In parallel experiments, this signal was comparable to the cDNA signal generated using oligo-dT (36 bases long) as a primer and is at least an order of magnitude greater than the signal generated from background non-specific IST signals produced from endogenous primer-template complexes. The aRNA produced from IST-generated cDNA contains sequences for IB15 (band at approximately 680 nucleotides) and actin was also determined. The variations in hybridization intensities reflect differences in the abundance of aRNAs encoding each of these molecules, as well as the differing amounts of radioactivity incorporated into aRNA for longer mRNAs versus shorter mRNAs. Background is minimal as shown by the lack of hybridization of aRNA to the pCD vector in the IB15 sample and the lack of binding to the DNA ladder. The actin and $G_s$ signals on the autoradiogram correspond to DNAs of 3 kilobases in length and longer, because the cDNAs encoding these proteins were not separated from the plasmid vector by restriction enzyme digestion and hence appear in multimer forms of the super-coiled plasmid.

Characterization of Amplification Products from a Single Cell

A schematic of the microinjection technique used to introduce the $T7_{57}$-oligonucleotide into individual Purkinje cells was prepared. The cerebellar primary culture provides access to identified Purkinje cells throughout their development to maturity by three weeks in vitro. The mature stage of an individual Purkinje cell is characterized by extensive dendritic outgrowth, expression of Purkinje-cell specific immunohistochemical markers, and endogenous pacemaker firing activity properties (Gruol et al., supra) comparable to Purkinje neurons of similar age in vivo.

The amount of radiolabel incorporated into aRNA obtained from single cell amplifications from individual Purkinje cells ranged from 30,000 to 300,000 cpm. The reasons for this variability are unclear, but may result from different amounts of first strand cDNA synthesis, variable success in regeneration of functional T7 RNA polymerase promoter site during the preparation of the cDNA template or partial degradation of the $T7_{57}$-oligonucleotide (Wickstrom, J. Biochem. Biophys. Methods 13: 97–102 (1986)). This low number of radioactive counts precluded the use of single cell aRNA as a probe to screen for specific low abundance mRNAs, yet was sufficient to serve as a probe for cerebellar RNA to gauge the complexity of the amplified material. The aRNA probe hybridized to poly(A)+ and total RNA isolated from the rat cerebellum. The specificity of this RNA signal is evident in the lack of hybridization of aRNA to *E. coli* total RNA and pBluescript DNA.

In addition to amplifying an entire population of A-mRNA using a single primer complex, degenerate primers have been utilized to amplify specific sequences for a specific class of mRNAs. In attempts to clone receptors that are part of the G-protein coupled receptor family, a T7-amplification oligonucleotide primer which uses a sequence common to all of these receptors was synthesized as the primer (rather than oligo-$dT_{15}$ which will prime a majority of mRNAs). The primer was used to prime cDNA synthesis from mRNA isolated from NG108-15 cells. This first strand cDNA was then processed as described above. The population of resultant aRNA molecules was less "complex" than that made using the T7-57 primer and contains sequences for the receptors of interest. As is the case for hybridization of specific probes to mRNA in Northern analyses, the generation of aRNAs specific to certain mRNAs is only limited by the specificity of the sequences used to prime cDNA synthesis. For degenerate primers, reference is made to Gould et al., Proc. Natl. Acad. Sci. U.S.A. 86: 1934–1938 (1989), which is incorporated herein by reference.

From the foregoing, it will be appreciated that novel techniques have been devised for the in vitro amplification of heterogeneous, complex populations of cDNA by generating cDNA with a primer containing a phage RNA polymerase promoter sequence. The technique is capable of greater than 80 to 1000 or more-fold molar amplification of starting cDNA. Amplified, anti-sense RNA (aRNA) produced by these techniques can be prepared that closely matches the size distribution of the parent cDNA. The amplified material contains heterogeneous sequences as determined by binding of aRNA to genomic Southern blots and specific Northern blots; additionally, detection of specific messages of various abundances in the amplified material can be performed.

Moreover, the spectrum of aRNA produced during amplification qualitatively reflects the population of cDNA from which it is produced. Since relative amounts of individual sequences present in cDNA represent (to a first approximation) their relative abundances in the transcribed RNA population and since aRNA production appears to be linear, the amount of a specific RNA in an aRNA population should reflect its abundance in the original RNA population. Given this, results from both aRNA-probed Southern blots and slot-blots of aRNA and cDNA probed with actin and G-protein cDNAs suggest that actin mRNA is considerably more abundant in rat cerebellum than any of the G-alpha mRNAs tested. Of greater interest is the finding that $G_s$-alpha produced a substantially higher hybridization signal than signals from the other G-alpha sequences tested. This is surprising because $G_s$-alpha protein levels are lower than those of other G-alpha subunits in a variety of tissues (Gilman, Ann. Rev. Biochem. 56: 615–649 (1987)), including brain (Gierschik et al., Proc. Natl. Acad. Sci. USA 83: 2258–2262 (1986)). Such high relative abundance of $G_s$-alpha mRNA has, however, been detected in other brain regions by in situ hybridization (Largent et al., Proc. Natl. Acad. Sci. USA 85: 2864–2868 (1988)) as well as in the NG108 neuronal cell line. These results are consistent with the hypothesis that unique control of regulation for $G_s$-alpha in rates of protein turnover and/or mRNA translation may exist (Largent et al., supra).

Although the foregoing invention has been described in some detail by way of illustration and example for purposes of clarity of understanding, it will be apparent that certain changes and modifications may be practiced within the scope of the appended claims.

sentation of specific nucleic acid messages within the sample and each nucleic acid message within the sample has been amplified simultaneously with an RNA polymerase and with a single primer linked to an RNA polymerase promoter.

2. The multi-gene expression profile of claim 1, wherein said amplified specific nucleic acid messages comprise aRNA.

3. The multi-gene expression profile of claim 1, wherein said amplified specific nucleic acid messages comprise cDNA.

4. The multi-gene expression profile of 1, wherein said amplified specific nucleic acid messages are hybridized to a hybridizing target.

5. The multi-gene profile of claim 4, wherein said amplified specific nucleic acid messages are hybridized to a hybridizing target by northern or Southern blot.

6. The multi-gene expression profile of claim 1, wherein said sample is a mammalian cell.

7. The multi-gene expression profile of claim 6, wherein said sample is a cell from brain, spleen, bone, heart, vascular tissue, lung, kidney, liver, pituitary, endocrine gland, lymph node, or tumor.

8. The multi-gene expression profile of claim 6, wherein said sample is a blood cell.

9. The multi-gene expression profile of claim 6, wherein same sample is a neural cell.

10. The multi-gene expression profile of claim 6, wherein said sample is a single cell.

11. A multi-gene expression profile of a sample comprising a collection of linearly amplified specific nucleic acid messages, wherein said amplified specific nucleic acid messages have been amplified simultaneously with an RNA polymerase and with a single primer linked to an RNA polymerase promoter.

---

---

We claim:

1. A multi-gene expression profile of a sample comprising a collection of linearly amplified specific nucleic acid messages, wherein said amplified specific nucleic acid messages each have an abundance which reflects the relative repre- 12. The multi-gene expression profile of claim 11, wherein said amplified specific nucleic acid messages are hybridized to a hybridizing target.

* * * * *

SEQUENCE LISTING

<160> NUMBER OF SEQ ID NOS: 2

<210> SEQ ID NO 1
<211> LENGTH: 57
<212> TYPE: DNA
<213> ORGANISM: Bacteriophage T7

<400> SEQUENCE: 1
aaacgacggc cagtgaattg taatacgact cactataggg cgttttttttt tttttt    57

<210> SEQ ID NO 2
<211> LENGTH: 42
<212> TYPE: DNA
<213> ORGANISM: Bacteriophage T7

<400> SEQUENCE: 2
aaacgacggc cagtgaattg taatacgact cactataggg cg    42